(12) United States Patent
Libbus et al.

(10) Patent No.: US 8,332,047 B2
(45) Date of Patent: Dec. 11, 2012

(54) SYSTEM AND METHOD FOR CLOSED-LOOP NEURAL STIMULATION

(75) Inventors: Imad Libbus, St. Paul, MN (US); Andrew P. Kramer, Stillwater, MN (US); Julia Moffitt, North Liberty, IA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1554 days.

(21) Appl. No.: 11/280,940

(22) Filed: Nov. 16, 2005

(65) Prior Publication Data

US 2006/0135998 A1 Jun. 22, 2006

Related U.S. Application Data

(63) Continuation-in-part of application No. 10/992,319, filed on Nov. 18, 2004.

(60) Provisional application No. 60/712,302, filed on Aug. 29, 2005.

(51) Int. Cl.
*A61N 1/05* (2006.01)
*A61N 1/36* (2006.01)
(52) U.S. Cl. .......................................... 607/117; 607/9
(58) Field of Classification Search .................. 607/36, 607/9, 117–118
See application file for complete search history.

(56) References Cited

U.S. PATENT DOCUMENTS

| 4,201,219 A | 5/1980 | Bozal Gonzalez |
| 4,791,931 A | 12/1988 | Slate |
| 5,111,815 A | 5/1992 | Mower |
| 5,190,035 A | 3/1993 | Salo et al. |
| 5,199,428 A | 4/1993 | Obel et al. |
| 5,203,326 A | 4/1993 | Collins |
| 5,243,980 A | 9/1993 | Mehra |
| 5,318,592 A | 6/1994 | Schaldach |
| 5,324,316 A | 6/1994 | Schulman et al. |
| 5,330,507 A | 7/1994 | Schwartz |

(Continued)

FOREIGN PATENT DOCUMENTS

EP 0481583 A2 4/1992

(Continued)

OTHER PUBLICATIONS

"U.S. Appl. No. 10/992,319, Non-Final Office Action mailed Oct. 5, 2007", OARN,14 pgs.

(Continued)

*Primary Examiner* — Niketa Patel
*Assistant Examiner* — Joseph Stoklosa
(74) *Attorney, Agent, or Firm* — Schwegman Lundberg & Woessner, P.A.

(57) ABSTRACT

Various device embodiments comprise a pulse generator, a signal processing module and a controller. The pulse generator is adapted to provide a neural stimulation signal to be applied at a neural simulation site within an autonomic nervous system (ANS). The signal processing module is adapted to receive and process sensed neural traffic at a neural sensing site within the ANS. The controller is connected to the pulse generator and adapted to provide a neural stimulation control signal to the pulse generator to generate the neural stimulation signal, and to the signal processing module to receive a feedback control signal indicative of the sensed neural traffic. The controller is adapted to adjust the neural stimulation control signal to adjust at least one parameter of the neural stimulation signal to converge on desired sensed neural traffic at the neural sensing site. Other aspects and embodiments are provided herein.

39 Claims, 20 Drawing Sheets

U.S. PATENT DOCUMENTS

| | | | |
|---|---|---|---|
| 5,356,425 A | 10/1994 | Bardy et al. | |
| 5,411,531 A | 5/1995 | Hill et al. | |
| 5,437,285 A | 8/1995 | Verrier et al. | |
| 5,507,784 A | 4/1996 | Hill et al. | |
| 5,522,854 A | 6/1996 | Ideker et al. | |
| 5,540,730 A | 7/1996 | Terry, Jr. et al. | |
| 5,578,061 A | 11/1996 | Stroetmann et al. | |
| 5,658,318 A | 8/1997 | Stroetmann et al. | |
| 5,676,686 A * | 10/1997 | Jensen et al. | 607/9 |
| 5,690,681 A | 11/1997 | Geddes et al. | |
| 5,700,282 A | 12/1997 | Zabara | |
| 5,727,558 A * | 3/1998 | Hakki et al. | 600/485 |
| 5,913,882 A | 6/1999 | King | |
| 5,916,239 A | 6/1999 | Geddes et al. | |
| 6,006,134 A | 12/1999 | Hill et al. | |
| 6,058,331 A | 5/2000 | King | |
| 6,073,048 A * | 6/2000 | Kieval et al. | 607/17 |
| 6,134,470 A | 10/2000 | Hartlaub | |
| 6,161,042 A | 12/2000 | Hartley et al. | |
| 6,164,284 A | 12/2000 | Schulman et al. | |
| 6,178,349 B1 | 1/2001 | Kieval | |
| 6,181,966 B1 | 1/2001 | Nigam | |
| 6,195,585 B1 | 2/2001 | Karunasiri et al. | |
| 6,240,314 B1 | 5/2001 | Plicchi et al. | |
| 6,240,316 B1 | 5/2001 | Richmond et al. | |
| 6,272,377 B1 | 8/2001 | Sweeney et al. | |
| 6,292,695 B1 | 9/2001 | Webster, Jr. et al. | |
| 6,371,922 B1 | 4/2002 | Baumann et al. | |
| 6,393,316 B1 | 5/2002 | Gillberg et al. | |
| 6,400,982 B2 | 6/2002 | Sweeney et al. | |
| 6,421,557 B1 | 7/2002 | Meyer | |
| 6,449,507 B1 | 9/2002 | Hill et al. | |
| 6,473,644 B1 | 10/2002 | Terry, Jr. et al. | |
| 6,487,450 B1 | 11/2002 | Chen | |
| 6,493,585 B2 | 12/2002 | Plicchi et al. | |
| 6,511,500 B1 | 1/2003 | Rahme | |
| 6,522,926 B1 | 2/2003 | Kieval et al. | |
| 6,532,388 B1 | 3/2003 | Hill et al. | |
| 6,542,774 B2 | 4/2003 | Hill et al. | |
| 6,564,096 B2 | 5/2003 | Mest | |
| 6,611,713 B2 | 8/2003 | Schauerte | |
| 6,622,041 B2 | 9/2003 | Terry, Jr. et al. | |
| 6,628,987 B1 | 9/2003 | Hill et al. | |
| 6,695,885 B2 | 2/2004 | Schulman et al. | |
| 6,804,561 B2 | 10/2004 | Stover | |
| 7,020,521 B1 | 3/2006 | Brewer et al. | |
| 7,123,961 B1 | 10/2006 | Kroll et al. | |
| 7,123,967 B2 | 10/2006 | Weinberg | |
| 7,149,574 B2 * | 12/2006 | Yun et al. | 607/2 |
| 7,260,431 B2 | 8/2007 | Libbus et al. | |
| 7,277,761 B2 | 10/2007 | Shelchuk | |
| 7,769,450 B2 | 8/2010 | Libbus et al. | |
| 7,783,353 B2 | 8/2010 | Libbus et al. | |
| 2002/0026221 A1 | 2/2002 | Hill et al. | |
| 2002/0026222 A1 | 2/2002 | Schauerte et al. | |
| 2002/0042637 A1 | 4/2002 | Stover | |
| 2002/0058877 A1 | 5/2002 | Baumann et al. | |
| 2002/0107553 A1 | 8/2002 | Hill et al. | |
| 2002/0107557 A1 | 8/2002 | Edell et al. | |
| 2002/0120304 A1 | 8/2002 | Mest | |
| 2002/0143369 A1 | 10/2002 | Hill et al. | |
| 2002/0165586 A1 | 11/2002 | Hill et al. | |
| 2003/0003052 A1 | 1/2003 | Hampton | |
| 2003/0004549 A1 | 1/2003 | Hill et al. | |
| 2003/0040774 A1 | 2/2003 | Terry et al. | |
| 2003/0045909 A1 | 3/2003 | Gross et al. | |
| 2003/0060848 A1 | 3/2003 | Keival et al. | |
| 2003/0060857 A1 | 3/2003 | Perrson et al. | |
| 2003/0060858 A1 | 3/2003 | Kieval et al. | |
| 2003/0078623 A1 | 4/2003 | Weinberg et al. | |
| 2003/0078629 A1 | 4/2003 | Chen | |
| 2003/0100924 A1 | 5/2003 | Foreman et al. | |
| 2003/0114905 A1 | 6/2003 | Kuzma | |
| 2003/0149450 A1 | 8/2003 | Mayberg | |
| 2003/0158584 A1 | 8/2003 | Cates et al. | |
| 2003/0195578 A1 | 10/2003 | Perron et al. | |
| 2003/0212440 A1 | 11/2003 | Boveja | |
| 2003/0212445 A1 | 11/2003 | Weinberg | |
| 2004/0019364 A1 * | 1/2004 | Kieval et al. | 607/9 |
| 2004/0131998 A1 | 7/2004 | Marom et al. | |
| 2004/0138517 A1 | 7/2004 | Osorio et al. | |
| 2004/0199210 A1 | 10/2004 | Shelchuk | |
| 2004/0210261 A1 | 10/2004 | King et al. | |
| 2004/0215263 A1 | 10/2004 | Virag et al. | |
| 2005/0085864 A1 | 4/2005 | Schulman et al. | |
| 2005/0096705 A1 | 5/2005 | Pastore et al. | |
| 2005/0143779 A1 | 6/2005 | Libbus | |
| 2005/0143785 A1 | 6/2005 | Libbus | |
| 2005/0149126 A1 | 7/2005 | Libbus | |
| 2005/0149127 A1 | 7/2005 | Libbus | |
| 2005/0149128 A1 | 7/2005 | Heil, Jr. et al. | |
| 2005/0149129 A1 | 7/2005 | Libbus et al. | |
| 2005/0149130 A1 | 7/2005 | Libbus | |
| 2005/0149131 A1 | 7/2005 | Libbus et al. | |
| 2005/0149132 A1 | 7/2005 | Libbus | |
| 2005/0149133 A1 | 7/2005 | Libbus et al. | |
| 2005/0149143 A1 | 7/2005 | Libbus et al. | |
| 2005/0149155 A1 | 7/2005 | Scheiner et al. | |
| 2005/0149156 A1 | 7/2005 | Libbus et al. | |
| 2005/0261741 A1 | 11/2005 | Libbus et al. | |
| 2005/0288718 A1 | 12/2005 | Sunagawa et al. | |
| 2006/0074451 A1 | 4/2006 | Chen et al. | |
| 2006/0106428 A1 | 5/2006 | Libbus et al. | |
| 2006/0106429 A1 | 5/2006 | Libbus et al. | |
| 2006/0116737 A1 | 6/2006 | Libbus | |
| 2007/0021799 A1 | 1/2007 | Kieval et al. | |
| 2007/0142864 A1 | 6/2007 | Libbus et al. | |
| 2008/0167694 A1 | 7/2008 | Bolea et al. | |
| 2008/0228238 A1 | 9/2008 | Libbus | |
| 2010/0286740 A1 | 11/2010 | Libbus et al. | |
| 2010/0286741 A1 | 11/2010 | Libbus et al. | |
| 2011/0082514 A1 | 4/2011 | Libbus et al. | |

FOREIGN PATENT DOCUMENTS

| | | | |
|---|---|---|---|
| EP | 0688578 | A1 | 12/1995 |
| EP | 0721786 | A2 | 7/1996 |
| WO | WO-2006055436 | A1 | 5/2006 |
| WO | WO-2006055849 | A1 | 5/2006 |
| WO | WO-2008/063396 | A1 | 5/2008 |

OTHER PUBLICATIONS

Andersen, H , "Long-term follow-up of patients from a randomised trial of atrial versus ventricular pacing for sick-sinus syndrome", *Lancet*, 350(9086), (Oct. 25, 1997),1210-6.

Benchimol, A , "Cardiac hemodynamics during stimulation of the right atrium, right ventricle, and left ventricle in normal and abnormal hearts", *Circulation*, 33(6), (Jun. 1966),933-44.

Bevan, J A., et al., "Postganglionic sympathetic delay in vascular smooth muscle", *Journal of Pharmacology & Experimental Therapeutics*, 152(2), (May 1966),221-30.

Bevan, J A., et al., "Sympathetic nerve-free vascular muscle", *Journal of Pharmacology & Experimental Therapeutics*, 157(1), (Jul. 1967),117-24.

Bilgutay, A M., "A new concept in the treatment of hypertension utilizing an implantable electronic device: "Baropacer"", *Trans Am Soc Artif Intern Organs.*, 10, (1964),387-395.

Bilgutay, A M., "Vagal tuning for the control of supraventricular arrhythmias", *Surgical Forum*, 16, (1965),151-3.

Bilgutay, Aydin M., "Vagal tuning. A new concept in the treatment of supraventricular arrhythmias, angina pectoris, and heart failure", *Journal of Thoracic and Cardiovascular Surgery*, 56(1), (Jul. 1968),71-82.

Borst, C , "Optimal frequency of carotid sinus nerve stimulation in treatment of angina pectoris", *Cardiovascular Research* ,8 (5) (Sep. 1974) ,674-80.

Braunwald, E , "Carotid sinus nerve stimulation in the treatment of angina pectoris and supraventricular tachycardia", *California Medicine*, 112(3), (Mar. 1970),41-50.

Braunwald, E ,"Relief of angina pectoris by electrical stimulation of the carotid-sinus nerves", *New England Journal of Medicine*, 277(24), (Dec. 14, 1967), 1278-83.

Chapleau, Mark W., "Contrasting effects of static and pulsatile pressure on carotid baroreceptor activity in dogs", *Circulation*, vol. 61, No. 5, (Nov. 1987), 648-658.

Chapleau, M W., "Neuro-cardiovascular regulation: from molecules to man. Introduction.", *Annals of the New York Academy of Sciences*, 940, (Jun. 2001),xiii-xxii.

Chapleau, Mark W., "Pulsatile activation of baroreceptors causes central facilitation of baroreflex", *American Journal Physiol Heart Circ Physiol*, (Jun. 1989),256: H1735-1741.

Coleridge, J C., et al., "Relationship between pulmonary arterial pressure and impulse activity in pulmonary arterial baroreceptor fibres", *Journal of Physiology*, 158 (Sep. 1961),197-205.

Coleridge, J C., "The distribution, connexions and histology of baroreceptors in the pulmonary artery, with some observations on the sensory innervation of the ductus arteriosus", *Journal of Physiology*,(May 1961),591-602.

Cooper, Terry B., et al., "Neural effects on sinus rate and atrioventricular conduction produced by electrical stimulation from a transvenous electrode catheter in the canine right pulmonary artery", *Circulation Research*, vol. 46, No. 1, Jan. 1980),48-57.

Courtice, G P., "Effect of frequency and impulse pattern on the non-cholinergic cardiac response to vagal stimulation in the toad, *Bufo marinus*", *Journal of the Autonomic Nervous System*, 48(3), (Aug. 1994),267-72.

Dart Jr., C H., "Carotid sinus nerve stimulation treatment of angina refractory to other surgical procedures", *Annals of Thoracic Surgery*, 11(4), (Apr. 1971),348-59.

De Landsheere, D , "Effect of spinal cord stimulation on regional myocardial perfusion assessed by positron emission tomography", *American Journal of Cardiology*, 69(14), (May 1, 1992),1143-9

Diedrich, A , "Analysis of raw microneurographic recordings based on wavelet de-noising technique and classification algorithm: wavelet analysis in Microneurography", *IEEE Transactions on Biomedical Engineering*, 50(1) (Jan. 2003),41-50.

Dunning, Arend J., "Electrostimulation of the Carotid Sinus Nerve in Angina Pectoris", *University Department of Medicine, Binnengasthuis, Amsterdam; Printed by Royal VanGorcum, Assen, Netherlands*, (1971),1-92.

Epstein, S E., "Treatment of angina pectoris by electrical stimulation of the carotid-sinus nerves", *New England Journal of Medicine*, 280(18), (May 1, 1969),971-8.

Farrehi, C , "Stimulation of the carotid sinus nerve in treatment of angina pectoris", *American Heart Journal*, 80(6), (Dec. 1970),759-65.

Feliciano, L , "Vagal nerve stimulation releases vasoactive intestinal peptide which significantly increases coronary artery blood flow", *Cardiovascular Research* ,40 (1), (Oct. 1998),45-55.

Fromer, M , "Ultrarapid subthreshold stimulation for termination of atrioventricular node reentrant tachycardia", *Journal of the American College of Cardiology*, 20(4), (Oct. 1992),879-83.

Grassi, Guido , "Baroreflex and non-baroreflex modulation of vagal cardiac control after myocardial infarction", *Am J Cardiol.*, 84(5), (Sep. 1, 1999),525-9.

Griffith, Lawrence S., et al., "Electrical Stimulation of the Carotid Sinus Nerve in Normotensive and Renal Hypertensive Dogs", *Circulation*, 28, (Jul.-Dec. 1963),730.

Henning, R J., "Effects of autonomic nerve stimulation, asynchrony, and load dP/dtmax and on dP/dtmin", *American Journal of Physiology*, 260(4 Pt 2), (Apr. 1991),H1290-8.

Henning, R J., "Vagal nerve stimulation increases right ventricular contraction and relaxation and heart rate", *Cardiovascular Research*, 32(5), (Nov. 1996),846-53.

Henning, R J., "Vagal stimulation attenuates sympathetic enhancement of left ventricular function", *American Journal of Physiology*, 258(5 Pt 2), (May 1990),H1470-5.

Hood Jr., W B., et al., "Asynchronous contraction due to late systolic bulging at left ventricular pacing sites", *American Journal of Physiology*, 217(1), (Jul. 1969),215-21.

Ishise, H , "Time course of sympathovagal imbalance and left ventricular dysfunction in conscious dogs with heart failure", *Journal of Applied Physiology*, 84(4), (Apr. 1998),1234-41.

Jessurun, G A., "Coronary blood flow dynamics during transcutaneous electrical nerve stimulation for stable angina pectoris associated with severe narrowing of one major coronary artery", *American Journal of Cardiology*, 82(8), erratum appears in Am J Cardiol Feb. 15, 1999;83(4):642,(Oct. 15, 1998),921-6.

Kandel, Eric R., et al., "Part VII: Arousal, Emotion, and Behavioral Homeostasis", *In: Principles of neural science*, New York : McGraw-Hill, Health Professions Division,(2000),966-969.

Karpawich, P. P., et al., "Altered cardiac histology following apical right ventricular pacing in patients with congenital atrioventricular block", *Pacing Clin Electrophysiol.*, 22(9) (Sep. 1999) ,1372-7

Leclercq, C , et al.,"Hemodynamic importance of preserving the normal sequence of ventricular activation in permanent cardiac pacing", *Am Heart J.*,129(6), (Jun. 1995),1133-41.

Li, Meihua , "Vagal nerve stimulation markedly improves long-term survival after chronic heart failure in rats", *Circulation*, 109(1), Epub 2003 Dec. 8, 2003,(Jan. 6, 2004),1-5.

Libbus, Imad , "Cardiac Rhythm Management Device With Neural Sensor", U.S. Appl. No. 10/992,320, filed Nov. 18, 2004, 65 pgs.

Libbus, I. , et al., "Method and Apparatus for Synchronizing Neural Simulation to Cardiac Cycles", U.S. Appl. No. 11/099,141, filed Apr. 5, 2005, 36 pgs.

Mannheimer, C , "Epidural spinal electrical stimulation in severe angina pectoris", *British Heart Journal*, 59 (1) Jan. 1988) ,56-61.

Mannheimer, C , "Transcutaneous electrical nerve stimulation (TENS) in angina pectoris", *Pain*, 26(3), (Sep. 1986),291-300.

Mannheimer, C , "Transcutaneous electrical nerve stimulation in severe angina pectoris", *European Heart Journal*, 3(4), (Aug. 1982),297-302.

Mazgalev, T N., "Autonomic modification of the atrioventricular node during atrial fibrillation: role in the slowing of ventricular rate", *Circulation*, 99(21), (Jun. 1, 1999),2806-14.

Millar-Craig, M W., et al., "Circadian variation of blood-pressure", *Lancet*, 1(8068), (Apr. 15, 1978),795-7.

Minisi, A J., et al., "Regional left ventricular deafferentation increases baroreflex Sensitivity following myocardial infarction", *Cardiovasc Res.*, 58(1), (Apr. 1, 2003),136-41.

Murphy, D F., "Intractable angina pectoris: management with dorsal column stimulation", *Medical Journal of Australia*, 146(5), (Mar. 2, 1987),260.

Neistadt, A , "Effects of electrical stimulation of the carotid sinus nerve in reversal of experimentally induced hypertension", *Surgery*, 61(6), (Jun. 1967),923-31.

Peters, T K., "Temporal and spatial summation caused by aortic nerve stimulation in rabbits. Effects of stimulation frequencies and amplitudes", *Journal of the Autonomic Nervous System*, 27(3), (Aug. 1989),193-205.

Peters, T K., "The principle of electrical carotid sinus nerve stimulation: a nerve pacemaker system for angina pectoris and hypertension therapy", *Annals of Biomedical Engineering*,8(4-6), 1980 ,445-58.

Philbin, D M., "Inappropriate shocks delivered by an ICD as a result of sensed potentials from a transcutaneous electronic nerve stimulation unit", *Pacing & Clinical Electrophysiology*, 21(10), (Oct. 1998),2010-1.

Prakash, P , "Asymmetrical distribution of aortic nerve fibers in the pig", *Anat Rec.*, 158(1), (May 1967),51-7.

Rosenqvist, M , "The effect of ventricular activation sequence on cardiac performance during pacing", *Pacing and Electrophysiology*19(9), (1996),1279-1286.

Rushmer, Robert F., "Chapter 5—Systemic Arterial Pressure", *In: Cardiovascular dynamics*, Philadelphia : Saunders,1976 ,176-216.

Schauerte, P , "Catheter stimulation of cardiac parasympathetic nerves in humans: a novel approach to the cardiac autonomic nervous system", *Circulation*, 104(20), (Nov. 13, 2001),2430-5.

Schauerte, Patrick N., et al., "Transvenous parasympathetic cardiac nerve stimulation: an approach for stable sinus rate control", *Journal of Cardiovascular Electrophysiology*,10(11), (Nov. 1999),1517-24.

Schauerte, Patrick N., "Transvenous Parasympathetic Nerve Stimulation in the Inferior Vena Cava and Atrioventricular Conduction", *Journal of Cardiovascular Electrophysiology*,11(1), (Jan. 2000),64-69.

Schauerte, P , "Ventricular rate control during atrial fibrillation by cardiac parasympathetic nerve stimulation: a transvenous approach", *Journal of the American College of Cardiology*, 34(7), (Dec. 1999),2043-50.

Scherlag, M A., "Endovascular Neural Stimulation Via a Novel Basket Electrode Catheter: Comparison of Electrode Configurations", *Journal of Interventional Cardiac Electrophysiology*, 4(1) (Apr. 2000),219-224.

Sigurdsson, Axel, "The role of neurohormonal activation in chronic heart failure and postmyocardial infarction", *American Heart Journal*,132 (1 Pt 2 Su), (Jul. 1996),229-234.

Takahashi, N , "Vagal modulation of ventricular tachyarrhythmias induced by left ansae subclaviae stimulation in rabbits", *Japanese Heart Journal*, 39(4), (Jul. 1998),503-11.

Tse, H F., et al., "Long-term effect of right ventricular pacing on myocardial perfusion and function", *J Am Coll Cardiol.* 29(4),(Mar. 15, 1997),744-9.

Vanoli, E. , "Vagal stimulation and prevention of sudden death in conscious dogs with a healed myocardial infarction", *Circulation Research*, 68(5), (May 1991),1471-81.

Vanoli, Emilio, "Vagal stimulation and prevention of sudden death in conscious dogs with a healed myocardial infarction", *Circulation Research*, vol. 68, No. 5, (May 1991),1471-1481.

Veerman, D P., et al., "Circadian profile of systemic hemodynamics", *Hypertension*, 26(1), (Jul. 1995),55-9.

Verity, M A., et al., "Plurivesicular nerve endings in the pulmonary artery", Nature, 211(48), (Jul. 30, 1966),537-8.

Verity, M , et al., "Pulmonary artery innervation: a morphopharmacologic correlation", *Proceedings of the Western Pharmacology Society*, 8, (1965) ,57-9.

Wallick, D W., "Selective AV nodal vagal stimulation improves hemodynamics during acute atrial fibrillation in dogs", *American Journal of Physiology—Heart & Circulatory Physiology*, 281(4), Oct. 2001,H1490-7.

Waninger, M S., "Electrophysiological control of ventricular rate during atrial fibrillation", *Pacing & Clinical Electrophysiology*, 23(8), (Aug. 2000),1239-44.

Wiggers, C J., et al., "The muscular reactions of the mammalian ventricles to artificial surface stimuli", *American Journal of Physiology*,(1925) ,346-378.

Yanagiya, Y. , et al., "Bionic epidural stimulation restores arterial pressure regulation during orthostasis", *J. Appl. Physiol*, 97(3), (Sep. 2004),984-90.

Zhang, Y , "Optimal ventricular rate slowing during atrial fibrillation by feedback AV nodal-selective vagal stimulation", *American Journal of Physiology—Heart& Circulatory Physiology*, 282(3), (Mar. 2002),H1102-10.

Zhou, X , "Prevention of high incidence of neurally mediated ventricular arrhythmias by afferent nerve stimulation in dogs", *Circulation*, 101(7), (Feb. 22, 2000),819-24.

"U.S. Appl. No. 10/992,319, Restriction Requirement mailed Jul. 2, 2008", 6 pgs.

"U.S. Appl. No. 10/992,319, Response filed Jan. 7, 2008 to Non-Final Office Action mailed Oct. 5, 2007", 15 pgs.

"U.S. Appl. No. 10/992,319, Non- Final Office Action mailed May 22, 2009", 9 pgs.

"U.S. Appl. No. 10/992,319, Final Office Action mailed Dec. 29, 2008", 6 pgs.

"U.S. Appl. No. 10/992,319, Response filed Mar. 30, 2009 to Final Office Action mailed Dec. 29, 2008", 11 pgs.

"U.S. Appl. No. 10/992,319, Response filed Aug. 21, 2009 to Non Final Office Action mailed May 22, 2009", 12 pgs.

"U.S. Appl. No. 10/992,319, Supplemental Response filed Jan. 17, 2008 to Non-Final Office Action mailed Oct. 5, 2007", 11 pgs.

"European Application Serial No. 05851890.3, Communication mailed Sep. 27, 2007", 3 pgs.

"European Application Serial No. 05851890.3, Office Action mailed May 19, 2008", 6 pgs.

"European Application Serial No. 05851890.3, Response filed Jan. 27, 2008 to Communication mailed Sep. 27, 2007", 22 pgs.

"European Application Serial No. 05851890.3, Summons to Oral Proceedings mailed Jul. 13, 2009", 6 pgs.

"U.S. Appl. No. 10/992,319, Advisory Action mailed Sep. 8, 2010", 3 pgs.

"U.S. Appl. No. 10/992,319, Appeal Brief filed Oct. 12, 2010", 33 pgs.

"U.S. Appl. No. 10/992,319, Notice of Panel Decision mailed Sep. 17, 2010", 2 pgs.

"U.S. Appl. No. 10/992,319, Response filed May 11, 2010 to Final Office Action mailed Jan. 11, 2010", 13 pgs.

"European Application Serial No. 05825864.1, Summons to Attend Oral Proceedings mailed Jul. 9, 2009", 4 pgs.

"European Application Serial No. 05825864.1, Minutes of Oral Proceedings mailed Dec. 15, 2009"7 pgs.

"European Application Serial No. 05825864.1, Communication mailed Sep. 11, 2007", 6 pgs.

"European Application Serial No. 05825864.1, Communication mailed May 19, 2008", 5 pgs.

"European Application Serial No. 05825864.1, Response filed Dec. 1, 2008 to Communication mailed May 19, 2008", 7 pgs.

"European Application Serial No. 05825864.1, Response filed Mar. 20, 2008 to Communication mailed Sep. 11, 2007", 12 pgs.

"European Application Serial No. 05851890.3; Minutes of Oral Proceedings mailed Dec. 15, 2009", 8 pgs.

"International Application Serial No. PCT/US2005/040988, International Search Report mailed Mar. 27, 2006", 4 pgs.

"International Application Serial No. PCT/US2005/040988, Written Opinion mailed Mar. 27, 2006", 6 pgs.

"International Application Serial No. PCT/US2005/042009, International Search Report mailed Mar. 27, 2006", 5 pgs.

"International Application Serial No. PCT/US2005/042009, Written Opinion mailed Mar. 27, 2006", 5 pgs.

"Japanese Application Serial No. 2007-543138, Amended Claims filed Nov. 12, 2008", (w/English Translation of Amended Claims), 13 pgs.

"Japanese Application Serial No. 2007-543316; Amended Claims filed Nov. 17, 2008", (w/English Translation of Amended Claims), 20 pgs.

"U.S. Appl. No. 10/992,320 Non Final Office Action Mailed Sep. 25, 2009", 13 pgs.

"U.S. Appl. No. 10/992,319, Final Office Action mailed Jan. 11, 2010", 8 pgs.

"U.S. Appl. No. 10/992,319, Preliminary Amendment filed Aug. 3, 2005", 4 pgs.

"U.S. Appl. No. 10/992,319, Response filed Aug. 4, 2008 to Restriction Requirement mailed Jul. 2, 2008", 8 pgs.

"U.S. Appl. No. 10/992,320, Non-Final Office Action mailed on Nov. 12, 2008", 10 pgs.

"U.S. Appl. No. 10/992,320, Response filed Feb. 12, 2009 to Non Final Office Action mailed Nov. 12, 2008", 14 pgs.

"U.S. Appl. No. 10/992,320, Response filed Jul. 21, 2008 to Final Office Action mailed Mar. 19, 2008", 11 pgs.

"U.S. Appl. No. 10/992,320, Non-Final Office Action Mailed Sep. 28, 2007", 9 pgs.

"U.S. Appl. No. 10/992,320, Response filed Dec. 28, 2007 to Non-Final Office Action mailed Sep. 28, 2007", 11 pages.

"U.S. Appl. No. 10/992,320. Final Office Action mailed Mar. 19, 2008", 9 pgs.

"U.S. Appl. No. 10/992,320, Examiner Interview Summary mailed Feb. 20, 2009", 2 pgs.

"U.S. Appl. No. 10/992,320, Examiner Interview Summary mailed Apr. 30, 2009", 2 pgs.

"U.S. Appl. No. 10/992,320, Examiner Interview Summary mailed May 12, 2009", 2 pgs.

"U.S. Appl. No. 10/992,320, Notice of Allowance mailed Mar. 30, 2010", 4 pgs.

"U.S. Appl. No. 10/992,320, Notice of Allowance mailed Apr. 30, 2009", 6 pgs.

"U.S. Appl. No. 10/992,320, Notice of Allowance mailed May 12, 2009", 8 pgs.

"U.S. Appl. No. 10/992,320, Notice of Allowance mailed Sep. 2, 2009", 5 Pgs.

"U.S. Appl. No. 10/992,320, Response filed Jan. 25, 2005 to Non Final Office Action mailed Sep. 25, 2009", 15 pgs.

"U.S. Appl. No. 10/992,320, Preliminary Amendment filed Nov. 18, 2004", 3 pgs.

"U.S. Appl. No. 10/992,319, Pre-Appeal Brief Request filed Jul. 9, 2010", 5 pgs.

US 7,583,997, 09/2009, Libbus (withdrawn)

* cited by examiner

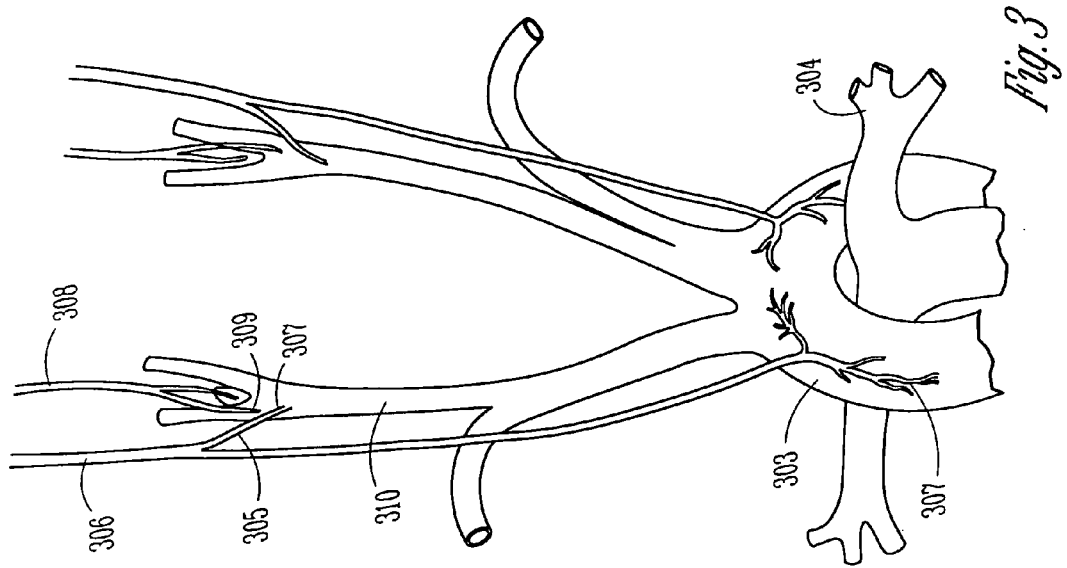
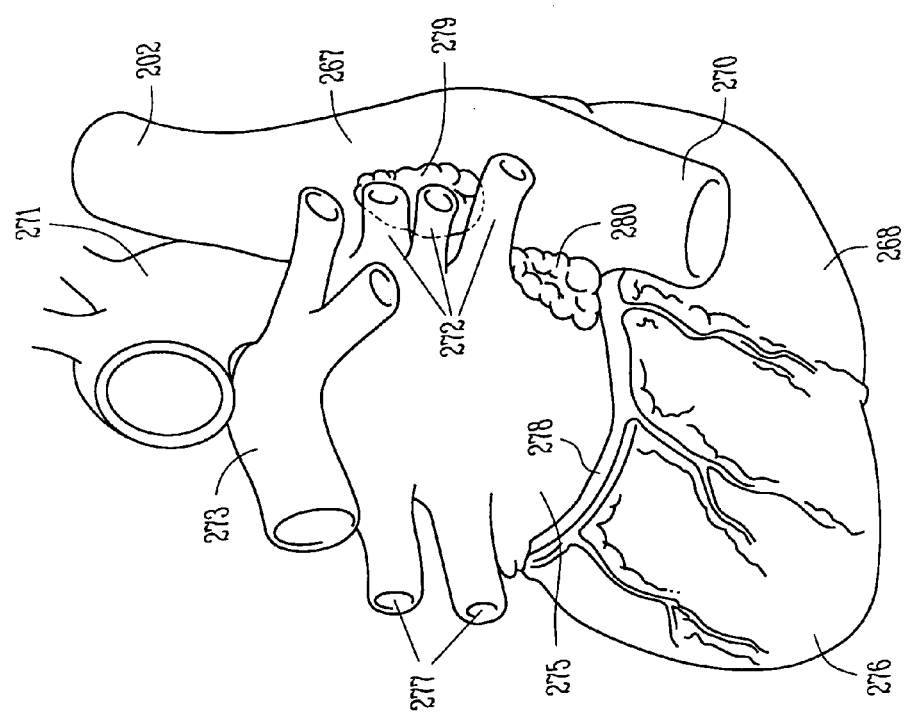

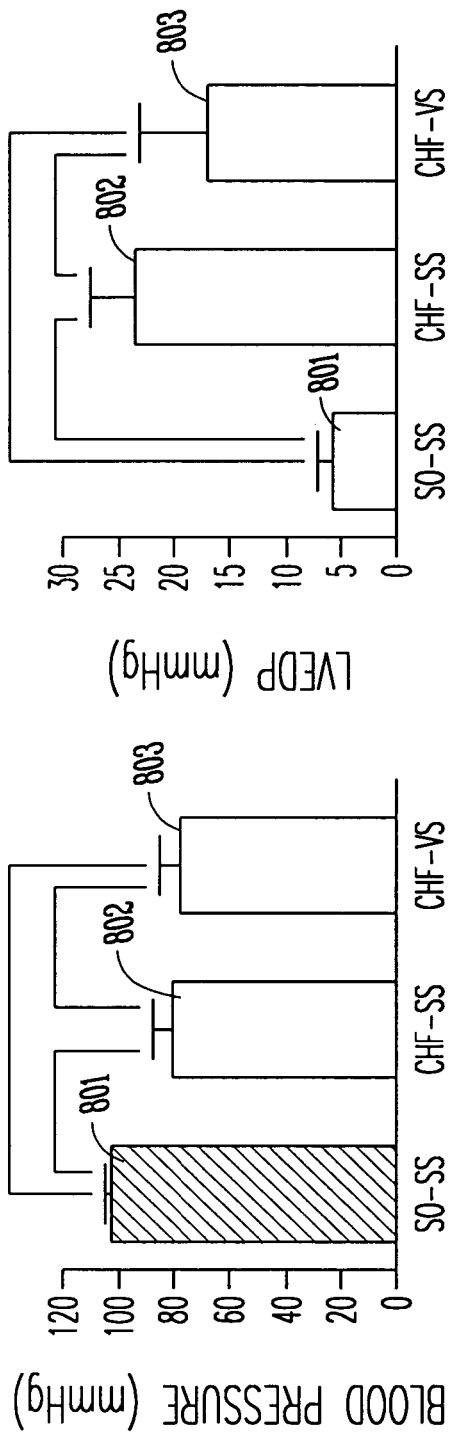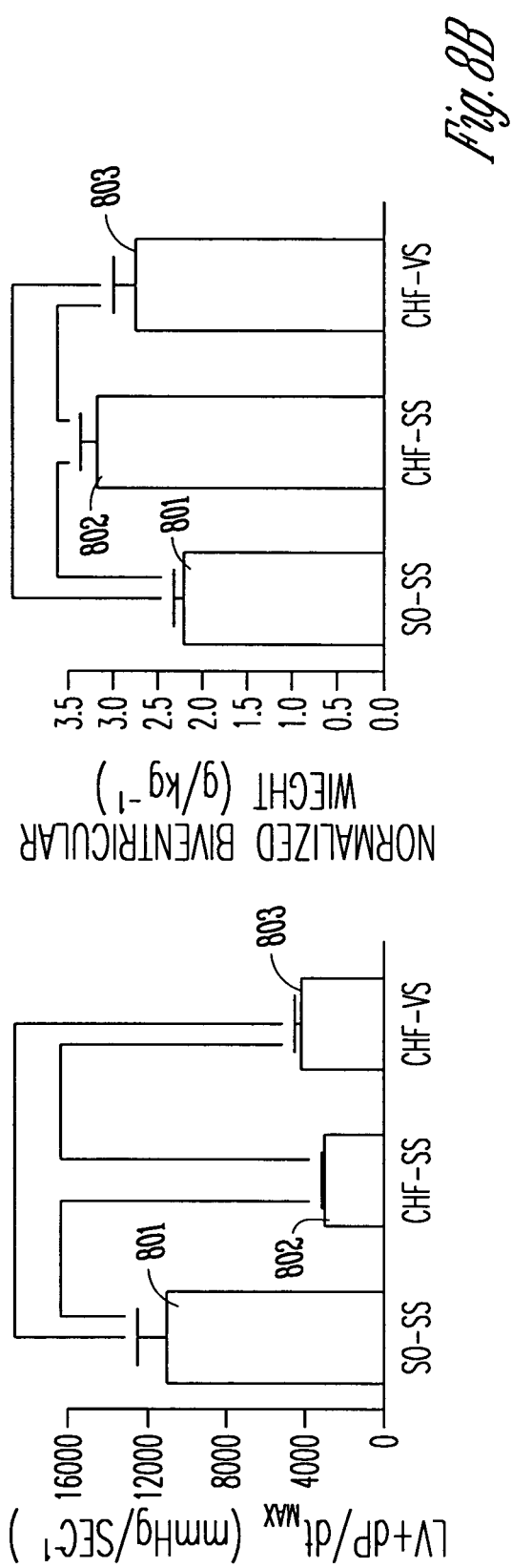
Fig. 8B

SYSTEM AND METHOD FOR CLOSED-LOOP NEURAL STIMULATION

CROSS REFERENCE TO RELATED APPLICATIONS

This application claims the benefit of U.S. Provisional Application No. 60/712,302, filed on Aug. 29, 2005, under 35 U.S.C. §119(e) and is a Continuation-In-Part of U.S. Ser. No. 10/992,319, filed on Nov. 18, 2004, the specifications of which are incorporated herein by reference in their entirety.

The following commonly assigned U.S. patent applications are related, and are herein incorporated by reference in their entirety: "Automatic Baroreflex Modulation Based on Cardiac Activity," Ser. No. 10/746,846, filed on Dec. 24, 2003; and "Cardiac Rhythm Management Device With Neural Sensor," Ser. No. 10/992,320, filed on Nov. 18, 2004.

TECHNICAL FIELD

This application relates generally to neural stimulation systems and, more particularly, to systems, devices and methods for sensing nerve traffic and providing closed-loop neural stimulation based on sensed nerve traffic.

BACKGROUND

Neural stimulators are used to treat a variety of disorders, such as epilepsy, obesity, and breathing disorders. Experimentally, neural stimulation has been shown to have a significant effect on several cardiovascular conditions, and has been proposed to treat hypertension, post myocardial infarction (MI) remodeling and heart failure.

Hypertension is a cause of heart disease and other related cardiac co-morbidities. Hypertension occurs when blood vessels constrict. As a result, the heart works harder to maintain flow at a higher blood pressure, which can contribute to heart failure. A large segment of the general population, as well as a large segment of patients implanted with pacemakers or defibrillators, suffer from hypertension. The long term mortality as well as the quality of life can be improved for this population if blood pressure and hypertension can be reduced. Many patients who suffer from hypertension do not respond to treatment, such as treatments related to lifestyle changes and hypertension drugs.

Direct electrical stimulation has been applied to afferent nerve trunks, including the vagus nerve and carotid sinus. Research has indicated that electrical stimulation of the carotid sinus nerve can result in reduction of experimental hypertension, and that direct electrical stimulation to the pressoreceptive regions of the carotid sinus itself brings about reflex reduction in experimental hypertension. Electrical systems have been proposed to treat hypertension in patients who do not otherwise respond to therapy involving lifestyle changes and hypertension drugs, and possibly to reduce drug dependency for other patients. The stimulation of sympathetic afferents triggers sympathetic activation, parasympathetic inhibition, vasoconstriction, and tachycardia. In contrast, parasympathetic activation results in bradycardia, vasodilation and inhibition of vasopressin release.

Neural stimulators that rely on continuous or intermittent open-loop stimulation do not adapt to physiologic changes during therapy.

SUMMARY

Various aspects of the present subject matter relate to a device. Various device embodiments comprise a pulse generator, a signal processing module and a controller. The pulse generator is adapted to provide a neural stimulation signal to be applied at a neural simulation site within an autonomic nervous system (ANS). The signal processing module is adapted to receive and process sensed neural traffic at a neural sensing site within the ANS. The controller is connected to the pulse generator and adapted to provide a neural stimulation control signal to the pulse generator to generate the neural stimulation signal, and to the signal processing module to receive a feedback control signal indicative of the sensed neural traffic. The controller is adapted to adjust the neural stimulation control signal to adjust at least one parameter of the neural stimulation signal to converge on desired sensed neural traffic at the neural sensing site.

Various aspects of the present subject matter relate to a method. According to various embodiments of the method, nerve traffic is sensed at a first autonomic nervous system (ANS) site. A feedback signal is generated that is indicative of at least one parameter derived from sensed nerve traffic at the first ANS site. A neural stimulation control signal with stimulation settings is generated using the feedback signal. A neural stimulation signal with a controlled neural stimulation intensity is generated at a second ANS site using the neural stimulation control signal.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

BRIEF DESCRIPTION OF THE DRAWINGS

FIGS. 2A-2C illustrate a heart.

FIG. 3 illustrates baroreceptors and afferent nerves in the area of the carotid sinuses and aortic arch.

FIGS. 8A-8C illustrate a known response of vagal nerve stimulation for rats with chronic heart failure (CHF), indicating that vagal nerve stimulation prevented pumping failure and cardiac remodeling and thus improved the long-term survival of CHF rats.

FIGS. 23A-D illustrate various control system embodiments for stimulating a parasympathetic afferent nerve.

DETAILED DESCRIPTION

Figure 1B:
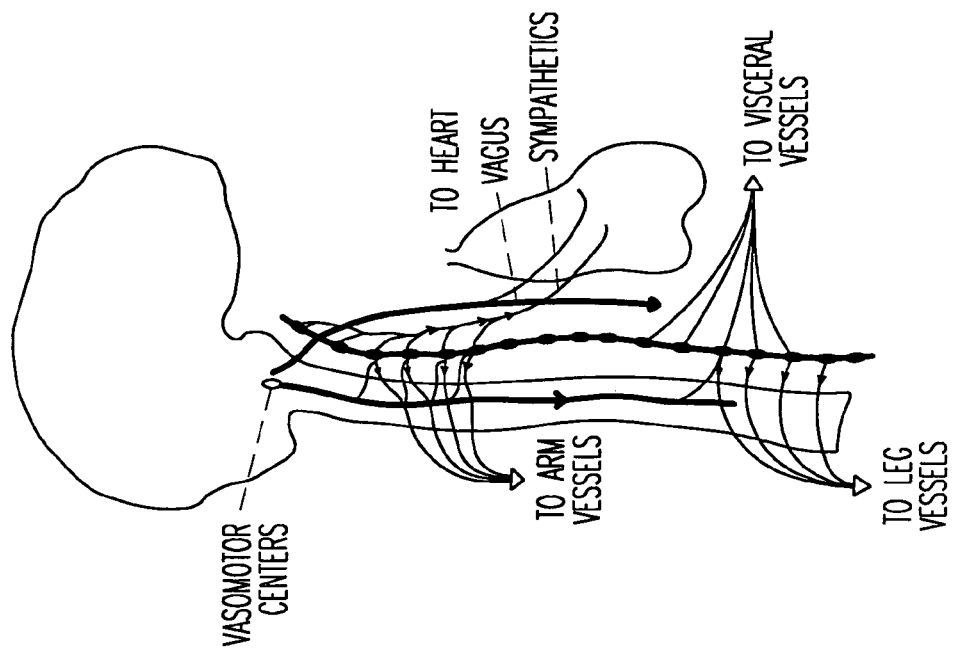
FIGS. 1A and 1B illustrate neural mechanisms for peripheral vascular control.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

A device is provided with at least one lead for use to perform neural sensing and neural stimulation functions. The device is able to amplify, filter, record and analyze the target nerve activity, and use the resulting information to accurately and appropriately deliver the neural stimulation. Sympathetic nerve activity (SNA) has a low signal amplitude (1-10 μV), and relatively high noise amplitude. Various embodiments provide amplification to provide a gain within a range of approximately 1,000 to approximately 99,000, for example, and bandpass filtering to pass frequencies within a range of approximately 30 Hz to approximately 3,000 Hz, to process neural traffic associated with SNA. Various embodiments use various subsets of these gain and frequency ranges.

Systems and methods are provided for monitoring nerve traffic for use to deliver appropriate neural stimulation. Monitored nerve traffic is used to accurately provide autonomic modulation for accurate and appropriate delivery of neural stimulation. Thus, the present subject mater provides a closed-loop neural stimulation system that allows the neural stimulation device to monitor nerve traffic and continuously provide appropriate therapy. A neural sensing lead is used to record nerve traffic from the peripheral nervous system (such as baroreceptors, afferent nerves and/or efferent nerves) to guide neural stimulation therapy, to record physiologic parameters such as pressure for diagnostic purposes, and/or to guide CRM therapy. Applications include a wide range of cardiovascular and non-cardiovascular diseases, such as hypertension, epilepsy, obesity, breathing disorders, and the like.

A brief description of hypertension and the baroreflex is provided below, followed by various systems to provide neural stimulation for hypertension or other therapies.

Hypertension and Baroreflex Physiology

A brief discussion of hypertension and the physiology related to baroreceptors is provided to assist the reader with understanding this disclosure. This brief discussion introduces hypertension, the autonomic nervous system, and the baroreflex.

Hypertension is a cause of heart disease and other related cardiac co-morbidities. Hypertension generally relates to high blood pressure, such as a transitory or sustained elevation of systemic arterial blood pressure to a level that is likely to induce cardiovascular damage or other adverse consequences. Hypertension has been arbitrarily defined as a systolic blood pressure above 140 mm Hg or a diastolic blood pressure above 90 mm Hg. Hypertension occurs when blood vessels constrict. As a result, the heart works harder to maintain flow at a higher blood pressure. Consequences of uncontrolled hypertension include, but are not limited to, retinal vascular disease and stroke, left ventricular hypertrophy and failure, myocardial infarction, dissecting aneurysm, and renovascular disease.

The autonomic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example.

The ANS includes, but is not limited to, the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system.

Figure 1A:
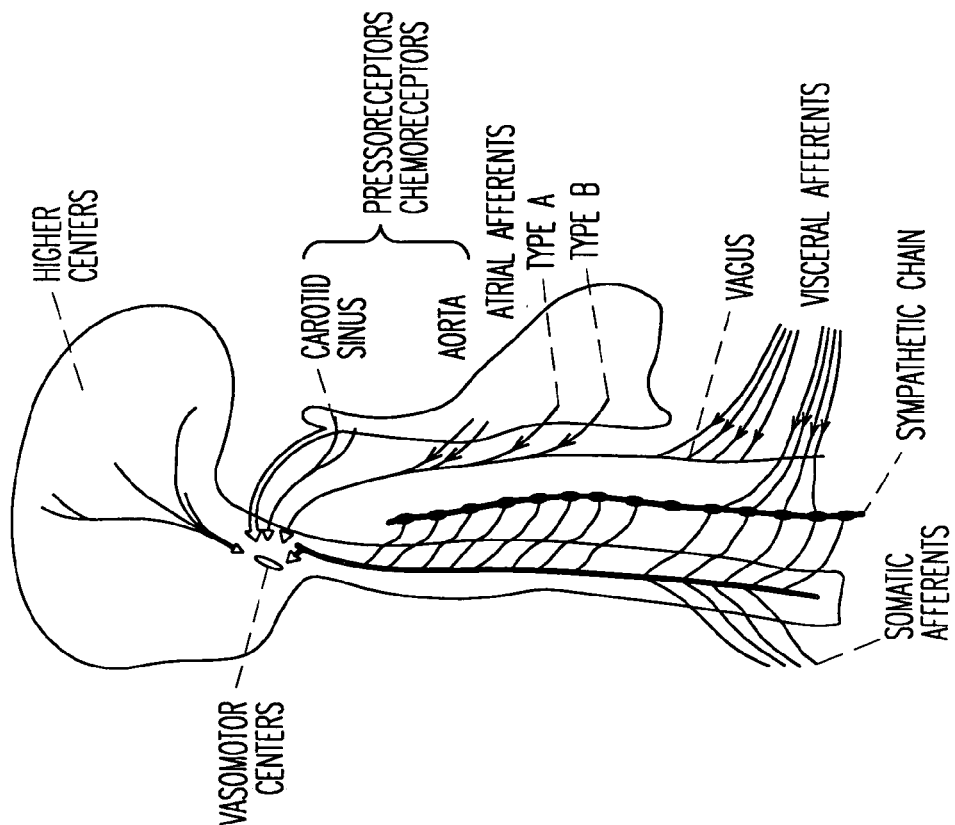

Various embodiments of the present subject matter provide neural stimulation to affect the heart rate, blood pressure, vasodilation and vasoconstriction. The heart rate and force is increased when the sympathetic nervous system is stimulated, and is decreased when the sympathetic nervous system is inhibited and the parasympathetic nervous system is stimulated. FIGS. 1A and 1B illustrate neural mechanisms for peripheral vascular control. FIG. 1A generally illustrates afferent nerves to vasomotor centers. An afferent nerve conveys impulses toward a nerve center. FIG. 1B generally illustrates efferent nerves from vasomotor centers. An efferent nerve conveys impulses away from a nerve center.

Stimulating the sympathetic and parasympathetic nervous systems can have effects other than heart rate and blood pressure. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system and/or inhibiting the sympathetic nervous system constricts the pupil, increases saliva and mucus production, contracts the bronchial muscle, increases secretions and motility in the stomach and large intestine, and increases digestion in the small intention, increases urine secretion, and contracts the wall and relaxes the sphincter of the bladder. The functions associated with the sympathetic and parasympathetic nervous systems are many and can be complexly integrated with each other. Thus, an indiscriminate stimulation of the sympathetic and/or parasympathetic nervous systems to achieve a desired response, such as vasodilation, in one physiological system may also result in an undesired response in other physiological systems.

A pressoreceptive region or field is capable of sensing changes in pressure, such as changes in blood pressure. Pressoreceptor regions are referred to herein as baroreceptors, which generally include any sensors of pressure changes. For example, baroreceptors include afferent nerves and further include sensory nerve endings that provide baroreceptor fields that are sensitive to the stretching of the wall that results from increased blood pressure from within, and function as the receptor of a central reflex mechanism that tends to reduce the pressure. The baroreflex functions as a negative feedback system, and relates to a reflex mechanism triggered by stimulation of a baroreceptor. Increased pressure stretches blood vessels, which in turn activates baroreceptors in the vessel walls. Activation of baroreceptors naturally occurs through internal pressure and stretching of the arterial wall, which excites the parasympathetic nervous system causing baroreflex inhibition of sympathetic nerve activity (SNA) and a reduction in systemic arterial pressure. An increase in baroreceptor activity induces a reduction of SNA, which reduces blood pressure by decreasing peripheral vascular resistance. Centrally mediated reflex pathways modulate cardiac rate, contractility and excitability. Baroreceptors and chemoreceptors in the heart, great vessels, and lungs, transmit neural signals reflective of cardiac activity through vagal and afferent fibers to the central nervous system. Chemoreceptors are also located within the carotid sinus. Thus, physiological parameters, such as systemic arterial pressure, can be determined based on nerve traffic. Such pressure information, for example, provides useful feedback information to guide CRM therapy such as CRT.

The baroreflex is a reflex triggered by stimulation of a baroreceptor. A baroreceptor includes any sensor of pressure changes, such as sensory nerve endings in the wall of the auricles of the heart, vena cava, aortic arch and carotid sinus, that is sensitive to stretching of the wall resulting from increased pressure from within, and that functions as the receptor of the central reflex mechanism that tends to reduce that pressure. Afferent nerves can also be electrically stimulated to induce the baroreflex, which inhibits the sympathetic nerve activity and stimulates parasympathetic nerve activity. Afferent nerve trunks, such as the vagus, aortic and carotid nerves, leading from the sensory nerve endings also form part of a baroreflex pathway. Stimulating a baroreflex pathway and/or baroreceptors inhibits sympathetic nerve activity, stimulates the parasympathetic nervous system and reduces systemic arterial pressure by decreasing peripheral vascular resistance and cardiac contractility. Baroreceptors are naturally stimulated by internal pressure and the stretching of vessel wall (e.g. arterial wall).

Embodiments of the present subject matter provide neural stimulation and receive sensed nerve traffic information to provide a closed-loop neural stimulator system with neural activity feedback. Some aspects of the present subject matter locally sense and/or stimulate specific nerve endings in vessel walls rather than or in addition to afferent and/or efferent nerve trunks. For example, some embodiments sense and/or stimulate baroreceptor sites or fields in the pulmonary artery. Some embodiments of the present subject matter involve sensing and/or stimulating baroreceptor sites or nerve endings in the aorta, the chambers of the heart, some embodiments of the present subject matter involve sensing and/or stimulating efferent pathways such as the fat pads of the heart, and some embodiments of the present subject matter involve sensing and/or stimulating an afferent nerve trunk, such as the vagus, carotid and aortic nerves. Various embodiments involve combinations of sensing and/or stimulating nerve endings, sensing efferent nerve pathways and sensing afferent nerve pathways. Some embodiments sense and/or stimulate nerve trunks using a cuff electrode, and some embodiments sense and/or stimulate nerve trunks using an intravascular lead positioned in a blood vessel proximate to the nerve. Examples of afferent nerve trunks include the vagus, aortic and carotid nerves. Examples of efferent nerve trunks include the cardiac branches off the vagus nerve. Stimulation of efferent nerves such as these cardiac branches or the nerves in cardiac fat pads conveys nervous impulses to an effector, and thus do not use the baroreflex negative feedback of the central nervous system, which responds to nerve activity on afferent nerves with nerve activity on efferent nerves. Some embodiments sense and/or stimulate neural traffic at any of the above-identified neural sites. Some embodiments stimulate efferent sympathetic nerve activity to treat hypotension, by providing specific efferent nerve branches that innervate specific target organs using a sensed activity corresponding to arterial blood pressure to provide a negative feedback closed loop control.

Figure 2B:
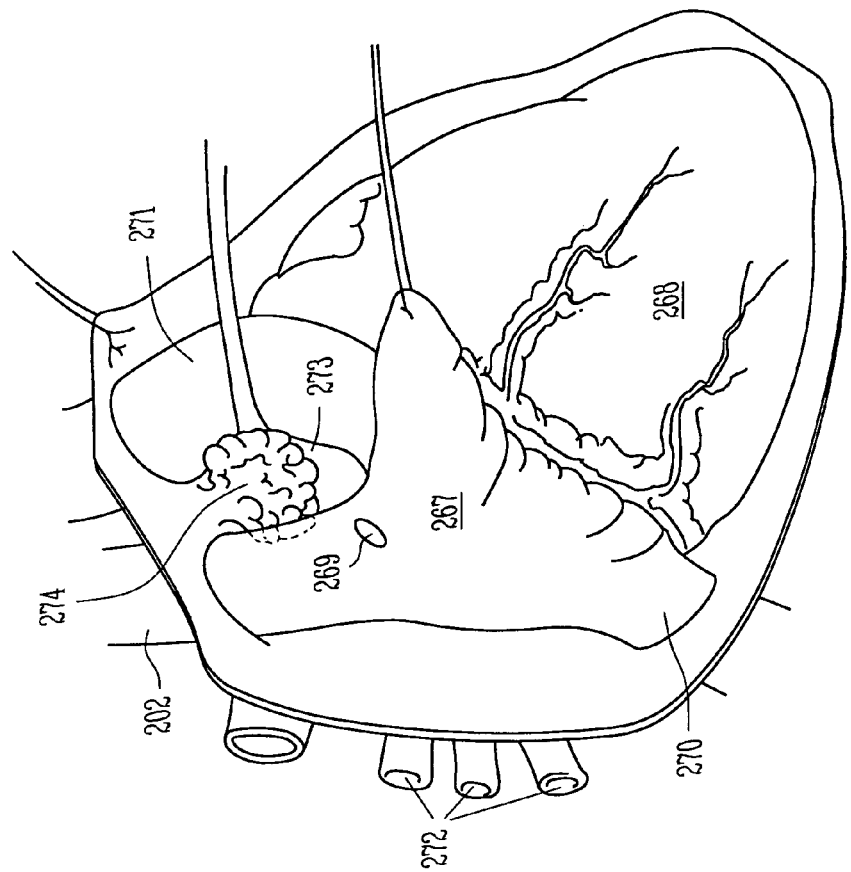
Figure 2A:
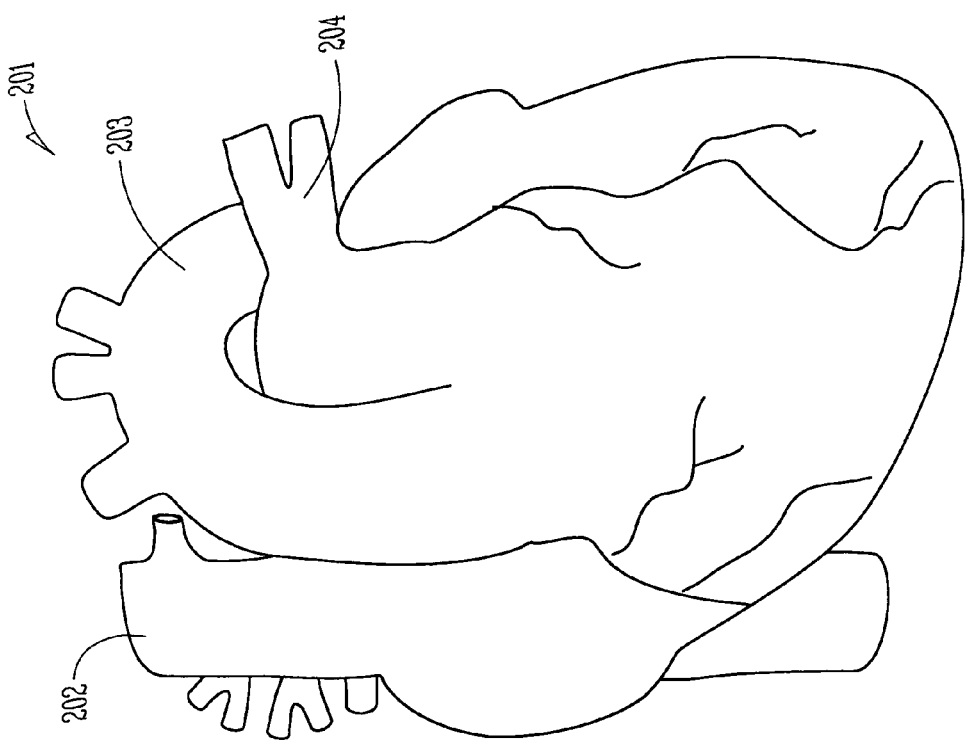

FIGS. 2A-2C illustrate a heart. As illustrated in FIG. 2A, the heart 201 includes a superior vena cava 202, an aortic arch 203, and a pulmonary artery 204, and is useful to provide a contextual relationship with the illustrations in FIGS. 3-5. As is discussed in more detail below, the pulmonary artery 204 includes baroreceptors. A lead is capable of being intravascularly inserted through a peripheral vein and through the tricuspid valve into the right ventricle of the heart (not expressly shown in the figure) similar to a cardiac pacemaker lead, and continue from the right ventricle through the pulmonary valve into the pulmonary artery. A portion of the pulmonary artery and aorta are proximate to each other. Various embodiments stimulate baroreceptors and/or sense neural activity by the baroreceptor in the aorta using a lead intravascularly positioned in the pulmonary artery. Thus, according to various aspects of the present subject matter, the baroreflex is stimulated and/or nerve activity is sensed in or around the pulmonary artery by at least one electrode intravascularly inserted into the pulmonary artery. In various embodiments, a wireless stimulating device, with or without pressure sensing capability, may be positioned via catheter into the pulmonary artery. Control of stimulation and/or energy for stimulation may be supplied by another implantable or external device via ultrasonic, electromagnetic or a combination thereof. Aspects of the present subject matter provide a relatively noninvasive surgical technique to implant a neural traffic sensor, with or without a baroreceptor stimulator, intravascularly into the pulmonary artery.

FIGS. 2B-2C illustrate the right side and left side of the heart, respectively, and further illustrate cardiac fat pads. FIG. 2B illustrates the right atrium 267, right ventricle 268, sinoatrial node 269, superior vena cava 202, inferior vena cava 270, aorta 271, right pulmonary veins 272, and right pulmonary artery 273. FIG. 2B also illustrates a cardiac fat pad 274 between the superior vena cava and aorta. Autonomic ganglia in the cardiac fat pad 274 are stimulated and/or nerve traffic is sensed in some embodiments using an electrode screwed or otherwise inserted into the fat pad, and are stimulated and/or nerve traffic is sensed in some embodiments using an intravenously-fed lead proximately positioned to the fat pad in a vessel such as the right pulmonary artery or superior vena cava, for example. FIG. 2C illustrates the left atrium 275, left ventricle 276, right atrium 267, right ventricle 268, superior vena cava 202, inferior vena cava 270, aorta 271, right pulmonary veins 272, left pulmonary vein 277, right pulmonary artery 273, and coronary sinus 278. FIG. 2C also illustrates a cardiac fat pad 279 located proximate to the right cardiac veins and a cardiac fat pad 280 located proximate to the inferior vena cava and left atrium. Autonomic ganglia in the fat pad 279 are stimulated and/or nerve traffic is sensed in some embodiments using an electrode screwed or otherwise inserted into the fat pad 279, and are stimulated and/or nerve traffic is sensed in some embodiments using an intravenously-fed lead proximately positioned to the fat pad in a vessel such as the right pulmonary artery 273 or right pulmonary vein 272, for example. Autonomic ganglia in the cardiac fat pad 280 are stimulated and/or nerve traffic is sensed in some embodiments using an electrode screwed or otherwise inserted into the fat pad, and are stimulated and/or nerve traffic is sensed in some embodiments using an intravenously-fed lead proximately positioned to the fat pad in a vessel such as the inferior vena cava 270 or coronary sinus or a lead in the left atrium 275, for example.

FIG. 3 illustrates baroreceptors in the area of the carotid sinus 305, aortic arch 303 and pulmonary artery 304. The aortic arch 303 and pulmonary artery 304 were previously illustrated with respect to the heart in FIG. 2A. As illustrated in FIG. 3, the vagus nerve 306 extends and provides sensory nerve endings 307 that function as baroreceptors in the aortic arch 303, in the carotid sinus 305 and in the common carotid artery 310. The glossopharyngeal nerve 308 provides nerve endings 309 that function as baroreceptors in the carotid sinus 305. These nerve endings 307 and 309, for example, are sensitive to stretching of the wall resulting from increased pressure from within. Activation of these nerve endings reduce pressure. Although not illustrated in the figures, the fat pads and the atrial and ventricular chambers of the heart also include baroreceptors. Cuffs have been placed around afferent nerve trunks, such as the vagal nerve, leading from baroreceptors to vasomotor centers to stimulate the baroreflex. According to various embodiments of the present subject matter, afferent nerve trunks can be stimulated using a cuff or intravascularly-fed lead positioned in a blood vessel proximate to the afferent nerves.

Figure 5:
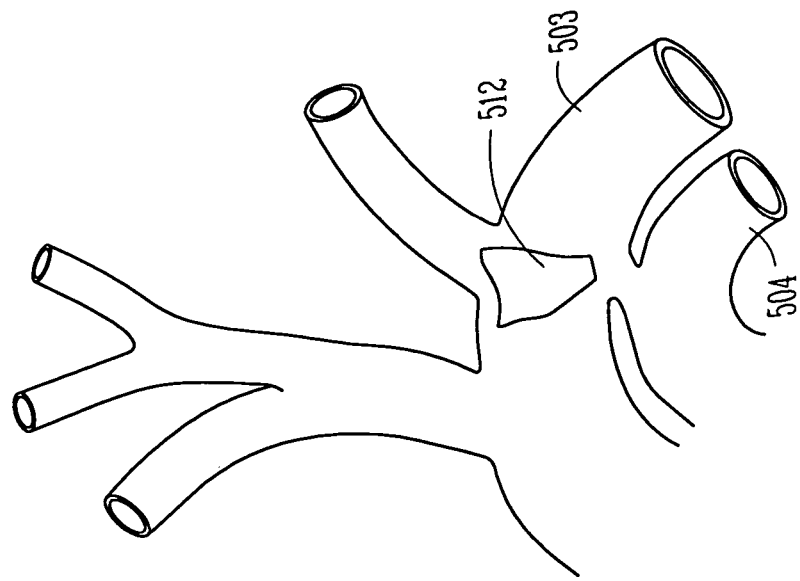
FIG. 5 illustrates baroreceptor fields in the aortic arch, the ligamentum arteriosum and the trunk of the pulmonary artery.
Figure 4:
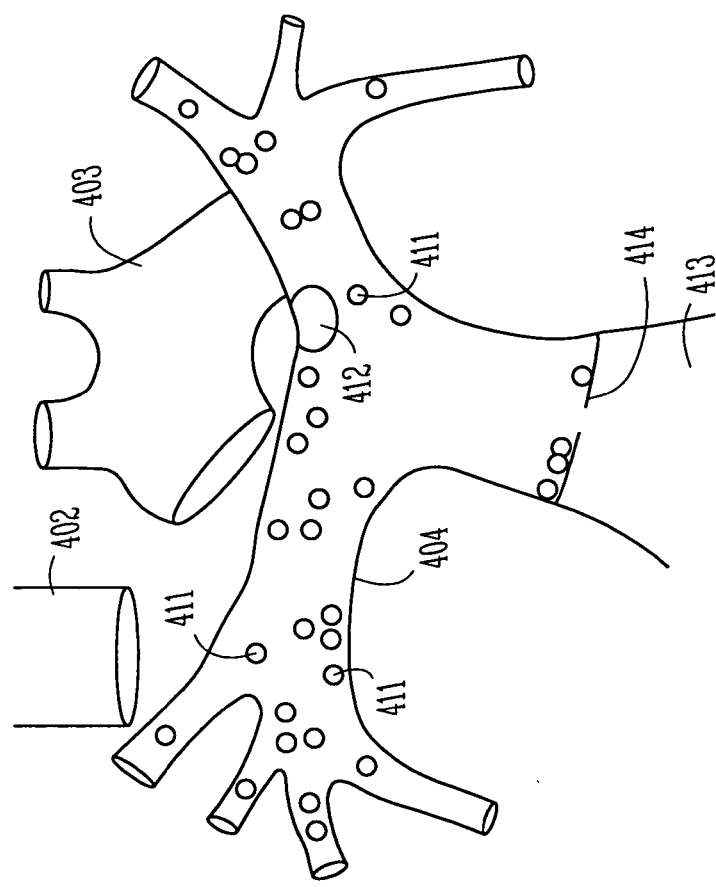
FIG. 4 illustrates baroreceptors in and around the pulmonary artery.

FIG. 4 illustrates baroreceptors in and around a pulmonary artery 404. The superior vena cava 402 and the aortic arch 403 are also illustrated. As illustrated, the pulmonary artery 404 includes a number of baroreceptors 411, as generally indicated by the dark area. Furthermore, a cluster of closely spaced baroreceptors is situated near the attachment of the ligamentum arteriosum 412. FIG. 4 also illustrates the right ventricle 413 of the heart, and the pulmonary valve 414 separating the right ventricle 413 from the pulmonary artery 404. According to various embodiments of the present subject matter, a lead is inserted through a peripheral vein and threaded through the tricuspid valve into the right ventricle, and from the right ventricle 413 through the pulmonary valve 414 and into the pulmonary artery 404 to stimulate baroreceptors in and/or around the pulmonary artery. In various embodiments, for example, the lead is positioned to stimulate the cluster of baroreceptors near the ligamentum arteriosum 412. FIG. 5 illustrates baroreceptor fields 512 in the aortic arch 503, near the ligamentum arteriosum and the trunk of the pulmonary artery 504. Some embodiments position the lead in the pulmonary artery to stimulate baroreceptor sites in the aorta and/or fat pads, such as are illustrated in FIGS. 2B-2C.

Figure 6:
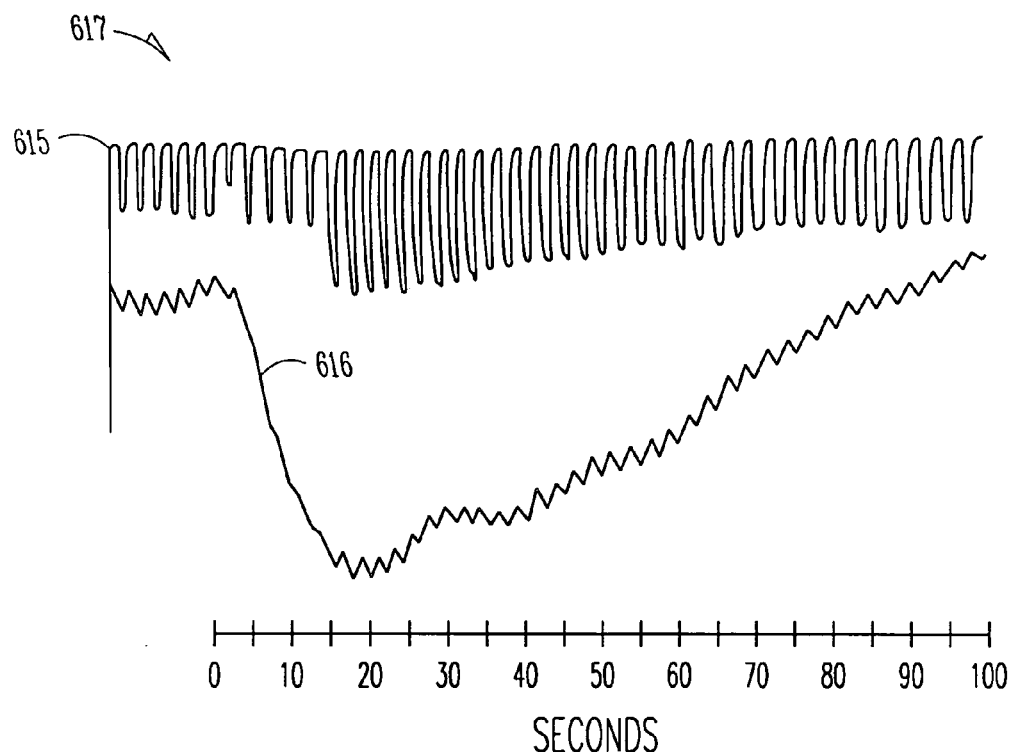
FIG. 6 illustrates a known relationship between respiration and blood pressure when the baroreflex is stimulated.

FIG. 6 illustrates a known relationship between respiration 615 and blood pressure 616 when the left aortic nerve is stimulated. When the nerve is stimulated at 617, the blood pressure 616 drops, and the respiration 615 becomes faster and deeper, as illustrated by the higher frequency and amplitude of the respiration waveform. The respiration and blood pressure appear to return to the pre-stimulated state in approximately one to two minutes after the stimulation is removed. This relationship between respiration and blood pressure allows respiration to be used as a surrogate parameter for blood pressure under some conditions.

Figure 7:
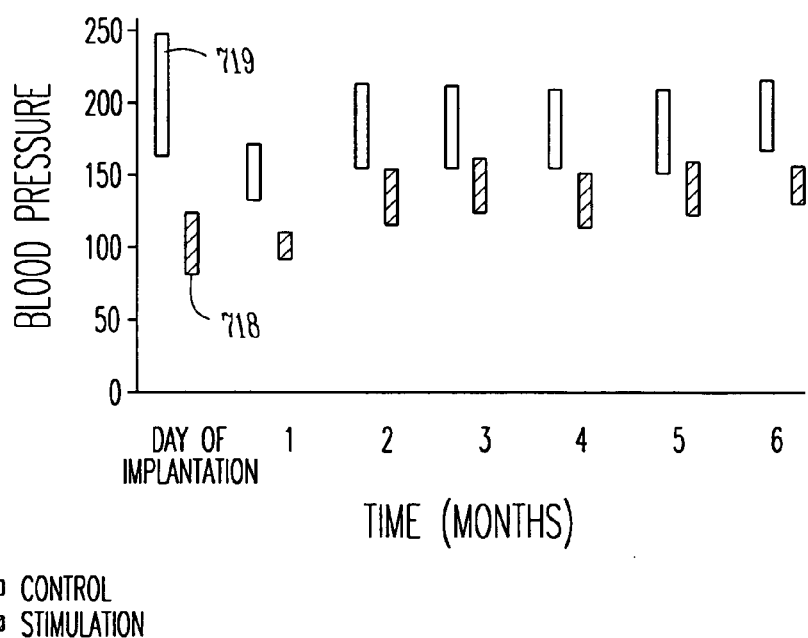
FIG. 7 illustrates a blood pressure response to carotid sinus nerve stimulation in a hypertensive dog during 6 months of intermittent carotid nerve stimulation.

FIG. 7 illustrates a known blood pressure response to carotid sinus nerve stimulation in a hypertensive dog during 6 months of intermittent carotid nerve stimulation. The carotid nerve stimulation involved turning on a carotid nerve stimulator once a month for up to six hours, and measuring the blood pressure response to monitor the stability of the acute response over long time periods. The figure illustrates that the blood pressure of a stimulated dog 718 is significantly less than the blood pressure of a control dog 719 that also has high blood pressure. Thus, such stimulation is capable of triggering the baroreflex to reduce high blood pressure.

Figure 8A:
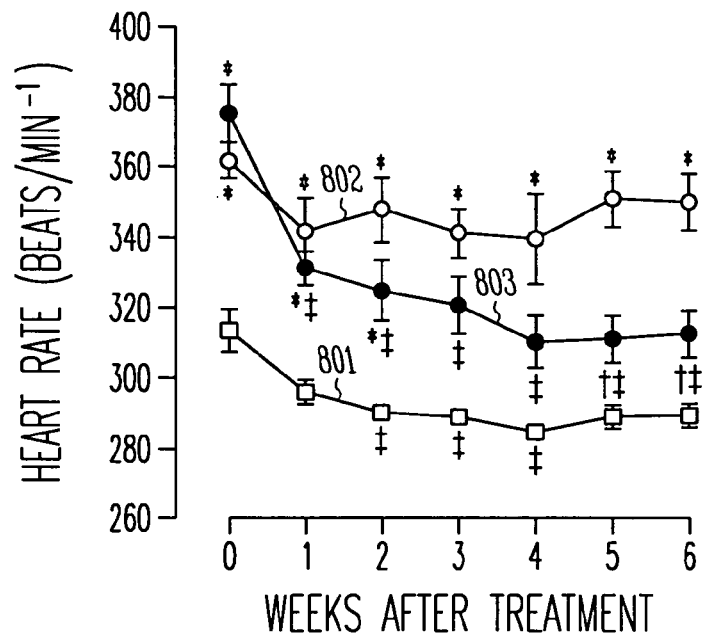
Figure 8C:
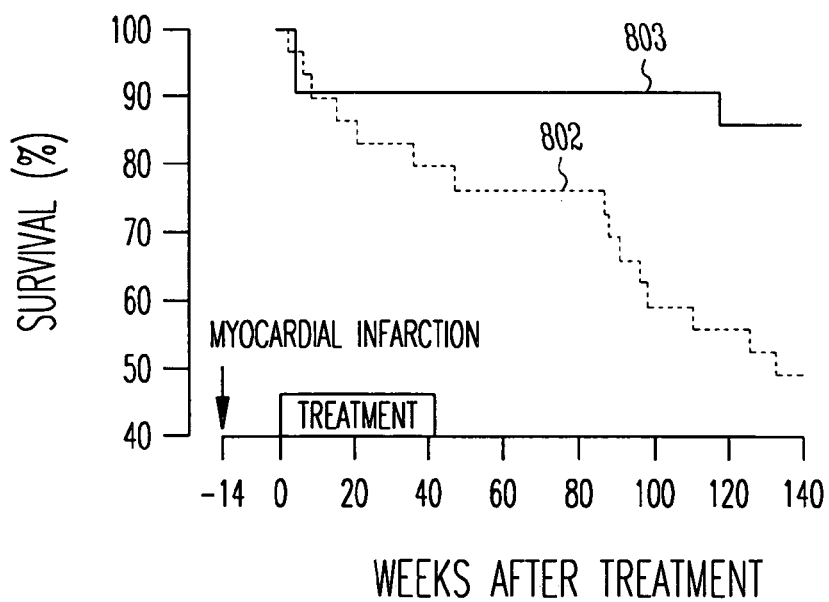

FIGS. 8A-8C illustrate a known response of vagal nerve stimulation for rats with chronic heart failure (CHF), indicating that vagal nerve stimulation prevented pumping failure and cardiac remodeling and thus improved the long-term survival of CHF rats in one study. Previous studies indicated that diminished cardiac vagal activity and increased heart rate predict a high mortality rate of CHF. Ligation of the left coronary artery of the rats induced CHF. Vagal stimulation (rectangular pulses of 0.2 ms duration at 20 Hz for 10 seconds every minute) was performed on some of the CHF rats. Other CHF rats were sham stimulated. Other rats were operated on without inducing CHF. FIGS. 8A-8C include graphs labeled with the numbers 801, 802 and 803, where 801 represents a control group of rats that were operated on without inducing CHF and that are not treated with vagal stimulation, where 802 represents a control group of CHF rats that were sham stimulated, and where 803 represents CHF rats treated with vagal stimulation. FIG. 8A illustrates average heart rates for rats without CHF 801, CHF rats with sham stimulation 802, and CHF rats with vagal stimulation 803. The rats with CHF 802 and 803 had a higher heart rate than the rats without CHF 801. CHF rats undergoing vagal stimulation 803 had significantly decreased heart rates in comparison to CHF rats with sham stimulation 802. FIG. 8B illustrates the effects of vagal nerve stimulation on mean blood pressure, left ventricular end-diastolic pressure (LVEDP), maximum rate of pressure change (dp/dt) of left ventricular pressure ($LV+dP/dt_{max}$), and normalized biventricular weight. FIG. 8B illustrates that the vagal stimulation improved pumping efficiency as evidenced by the lower LVEDP and higher $LV+dP/dt_{max}$ for vagal-stimulated rats 803 compared to sham-stimulated rats 802, and further illustrates that the vagal stimulation decreased the normalized biventricular weight for vagal-stimulated rats 803 compared to sham-stimulated rats 802. FIG. 8C illustrates that vagal nerve stimulation suppressed the mortality rate of CHF rats, as evidenced by the higher survival rate of the vagal-stimulated CHF rats 803 in comparison to the sham-stimulated CHF rats 802.

Systems to Provide Neural Stimulation

Examples of neural stimulators include anti-hypertension (AHT) devices or AHT components that are used to treat hypertension. Various embodiments of the present subject matter include stand-alone implantable neural stimulator systems, and include implantable devices that have integrated NS and cardiac rhythm management (CRM) components, and include systems with at least one implantable NS device and an implantable CRM device capable of communicating with each other either wirelessly or through a wire lead connecting the implantable devices. Although implantable systems are illustrated and discussed, various aspects and embodiments of the present subject matter can be implemented in external devices.

Figure 9A:
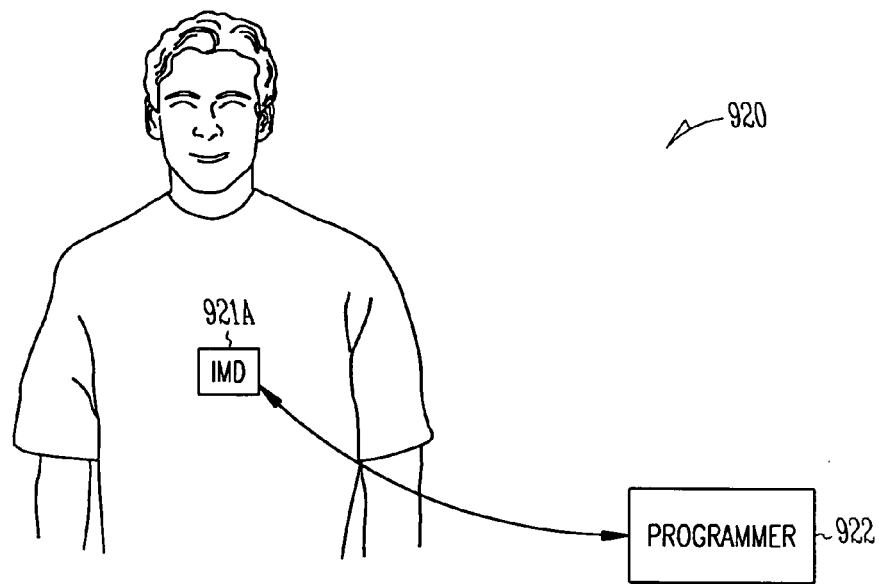
FIG. 9A illustrates a system including an implantable medical device (IMD) and a programmer, according to various embodiments of the present subject matter.

FIG. 9A illustrates a system 920 including an implantable medical device (IMD) 921A and a programmer 922, according to various embodiments of the present subject matter. Various embodiments of the IMD 921A include neural stimulator functions only, various embodiments include CRM functions only, and various embodiments include a combination of NS and CRM functions. Examples of cardiac stimulators include implantable cardiac rhythm management (CRM) devices such as pacemakers, implantable cardiac defibrillators (ICDs), and implantable devices capable of performing pacing and defibrillating functions. Implantable CRM devices provide electrical stimulation to selected chambers of the heart in order to treat disorders of cardiac rhythm. An implantable pacemaker, for example, is a CRM device that paces the heart with timed pacing pulses. The pacing pulses can be timed from other pacing pulses or sensed electrical activity. If functioning properly, the pacemaker makes up for the heart's inability to pace itself at an appropriate rhythm in order to meet metabolic demand by enforcing a minimum heart rate. Some CRM devices synchronize pacing pulses delivered to different areas of the heart in order to coordinate the contractions. Coordinated contractions allow the heart to pump efficiently while providing sufficient cardiac output.

Some Embodiments of the Neural Stimulator Provide AHT Neural Stimulation Functions to Treat Hypertension.

The programmer 922 and the IMD 921A are capable of wirelessly communicating data and instructions. In various embodiments, for example, the programmer 922 and IMD 921A use telemetry coils to wirelessly communicate data and instructions. Thus, the programmer can be used to adjust the programmed therapy provided by the IMD 921A, and the IMD can report device data (such as battery and lead resistance) and therapy data (such as sense and stimulation data) to the programmer using radio telemetry, for example. According to various embodiments, the IMD 921A stimulates baroreceptors to provide NS therapy such as AHT therapy. Various embodiments of the IMD 921A stimulate baroreceptors in the pulmonary artery using a lead fed through the right ventricle similar to a cardiac pacemaker lead, and further fed into the pulmonary artery. Other embodiments stimulate other baroreceptor sites or baroreflex pathways or combinations thereof, such as illustrated and described with respect to FIGS. 2A-2C, 3 and 4. According to various embodiments, the IMD 921A includes a sensor to sense ANS activity. Such a sensor can be used to perform feedback in a closed-loop control system. For example, various embodiments sense surrogate parameters, such as respiration and blood pressure, indicative of ANS activity. According to various embodiments, the IMD further includes cardiac stimulation capabilities, such as pacing, cardiac resynchronization therapy (CRT) and defibrillating capabilities in addition to the capabilities to stimulate baroreceptors and/or sense ANS activity. In some embodiments, the illustrated IMD includes two or more devices capable of communicating with each other via wireless technology; and in some embodiments, the illustrated IMD includes two or more devices capable of communicating with each other via a cable or wire, such as an intravenously fed lead.

Figure 9B:
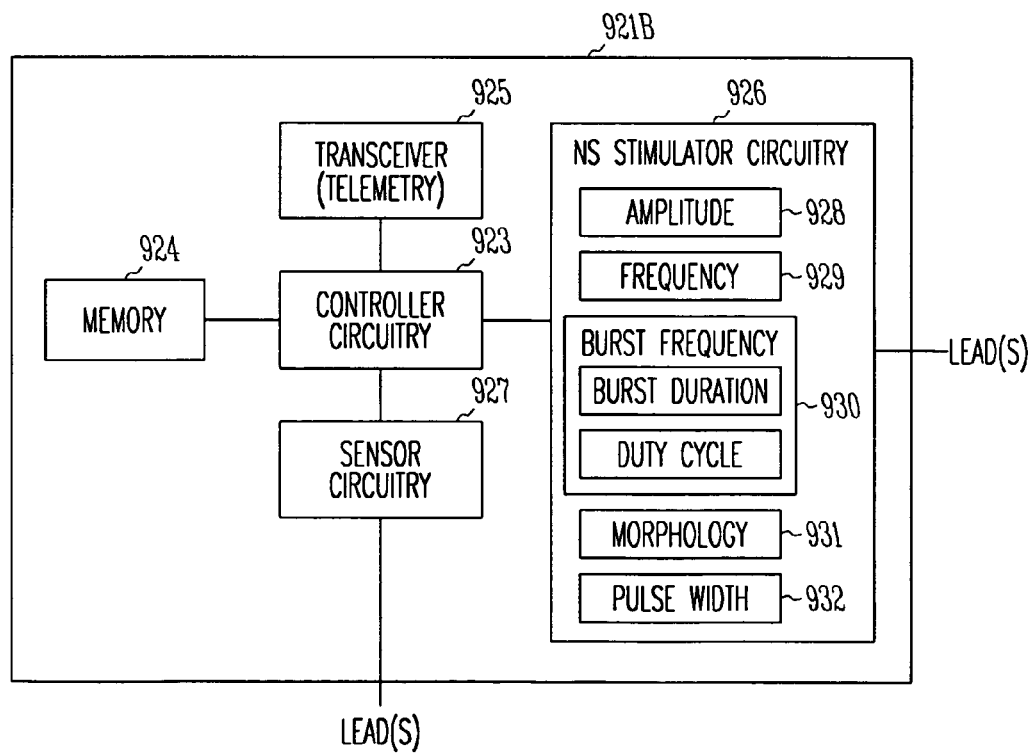
FIG. 9B illustrates an implantable medical device (IMD) such as the IMD shown in the system of FIG. 9A, according to various embodiments of the present subject matter.

FIG. 9B illustrates an implantable medical device (IMD) 921B such as the IMD 921A shown in the system 920 of FIG. 9A, according to various embodiments of the present subject matter. The illustrated IMD 921B performs NS functions. Some embodiments of the illustrated IMD 921B performs an AHT function, and thus illustrates an implantable AHT device. The illustrated device 921B includes controller circuitry 923 and a memory 924. The controller circuitry 923 is capable of being implemented using hardware, software, and combinations of hardware and software. For example, according to various embodiments, the controller circuitry 923 includes a processor to perform instructions embedded in the memory 924 to perform functions associated with NS therapy such as AHT therapy. For example, the illustrated device 921B further includes a transceiver 925 and associated circuitry for use to communicate with a programmer or another external or internal device. Various embodiments have wireless communication capabilities. For example, some transceiver embodiments use a telemetry coil to wirelessly communicate with a programmer or another external or internal device.

The illustrated device 921B further includes baroreceptor stimulation circuitry 926. Various embodiments of the device 921B also includes sensor circuitry 927. One or more leads are able to be connected to the sensor circuitry 927 and baroreceptor stimulation circuitry 926. The baroreceptor stimulation circuitry 926 is used to apply electrical stimulation pulses to desired baroreceptors sites, such as baroreceptor sites in the pulmonary artery, through one or more stimulation electrodes. The sensor circuitry 927 is used to detect and process ANS nerve activity. In various embodiments, the sensor circuitry is further used to detect and process surrogate parameters such as blood pressure, respiration and the like, to determine the ANS activity.

According to various embodiments, the stimulator circuitry 926 includes modules to set or adjust any one or any combination of two or more of the following pulse features: the amplitude 928 of the stimulation pulse, the frequency 929 of the stimulation pulse, the burst frequency 930 of the pulse, the wave morphology 931 of the pulse, and the pulse width 932. The illustrated burst frequency 930 pulse feature includes burst duration and duty cycle, which can be adjusted as part of a burst frequency pulse feature or can be adjusted separately. For example, a burst frequency can refer to the number of bursts per minute. Each of these bursts has a burst duration (an amount of time bursts of stimulation are provided) and a duty cycle (a ratio of time where stimulation is provided to total time). Thus, by way of example and not limitation, six bursts can be delivered during a one minute stimulation time (burst duration), where the length (pulse width) of each burst is five seconds and the time period between bursts is five seconds. In this example, the burst frequency is six burst per minute, the burst duration is 60 seconds, and the duty cycle is 50% ((6 bursts×5 sec./burst)/60 seconds). Additionally, the duration of one or more bursts can be adjusted without reference to any steady burst frequency. For example, a single stimulation burst of a predetermined burst duration or a pattern of bursts of predetermined pulse width(s) and burst timing can be provided in response to a sensed signal. Furthermore, the duty cycle can be adjusted by adjusting the number of bursts and/or adjusting the duration of one or more bursts, without requiring the bursts to be delivered with a steady burst frequency. Examples of wave morphology include a square wave, triangle wave, sinusoidal wave, and waves with desired harmonic components to mimic white noise such as is indicative of naturally-occurring baroreflex stimulation. Additionally, various controller embodiments are capable of controlling a duration of the stimulation.

Figure 10:
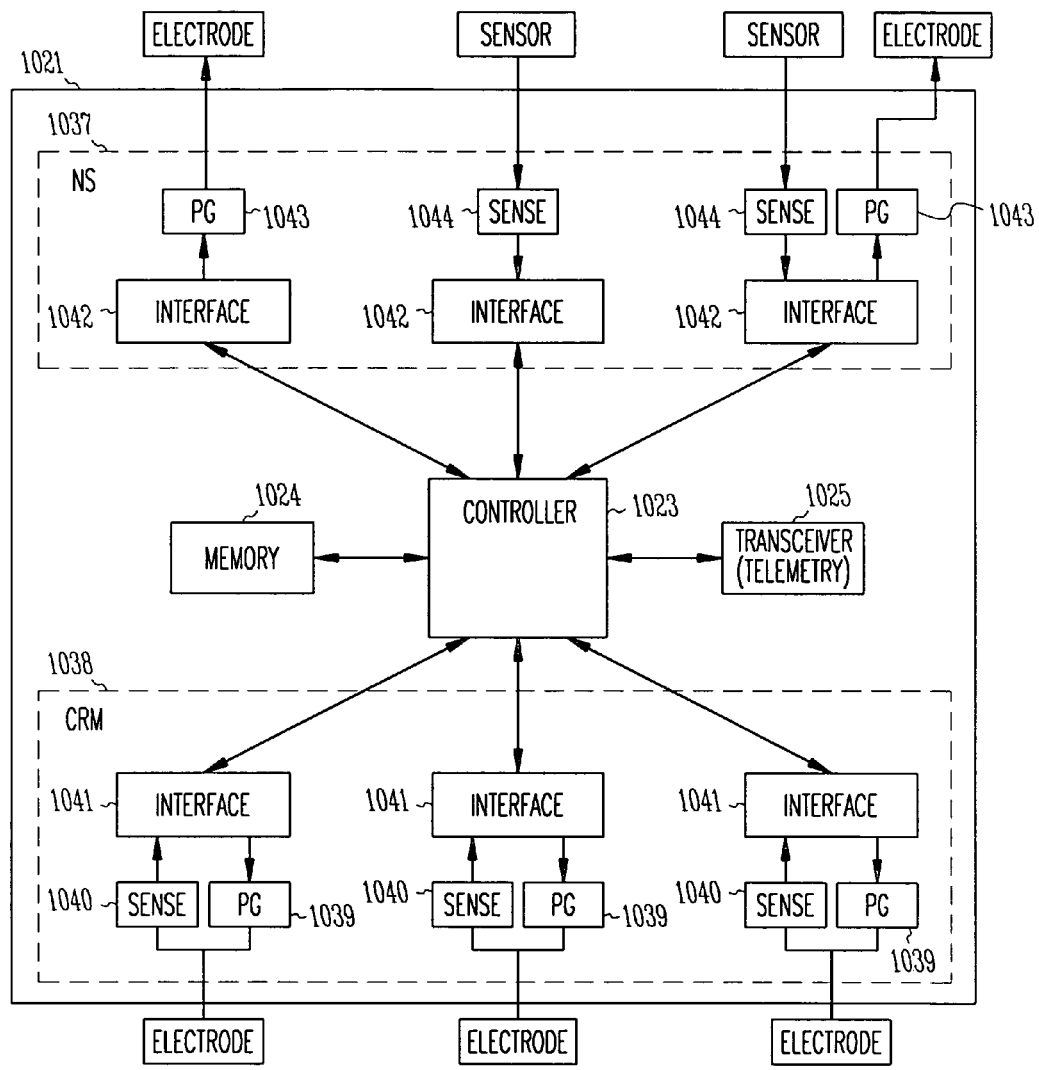
FIG. 10 illustrates an implantable medical device (IMD) such as shown in FIG. 8 having a neural stimulator (NS) component and cardiac rhythm management (CRM) component, according to various embodiments of the present subject matter.

FIG. 10 illustrates an implantable medical device (IMD) such as shown in FIG. 9A having a neural stimulator (NS) component and cardiac rhythm management (CRM) component, according to various embodiments of the present subject matter. Various IMD embodiments do not include a CRM component, as illustrated in FIG. 10. The illustrated device 1021 includes a controller 1023 and a memory 1024. According to various embodiments, the controller 1023 includes hardware, software, or a combination of hardware and software to perform the neural stimulation and CRM functions. Examples of CRM functions include, for example, pacing, defibrillating, and cardiac resynchronization therapy (CRT) functions. For example, the programmed therapy applications discussed in this disclosure are capable of being stored as computer-readable instructions embodied in memory and executed by a processor. According to various embodiments, the controller 1023 includes a processor to execute instructions embedded in memory to perform the baroreceptor stimulation and CRM functions. The illustrated device 1021 further includes a transceiver 1025 and associated circuitry for use to communicate with a programmer or another external or internal device. Various embodiments include a telemetry coil.

The CRM therapy section 1038 includes components, under the control of the controller, to stimulate a heart and/or sense cardiac signals using one or more electrodes. The CRM therapy section includes a pulse generator 1039 for use to provide an electrical signal through an electrode to stimulate a heart, and further includes sense circuitry 1040 to detect and process sensed cardiac signals or otherwise detect pulsatile parameters according to the present subject matter. An interface 1041 is generally illustrated for use to communicate between the controller 1023 and the pulse generator 1039 and sense circuitry 1040. Three electrodes are illustrated as an example for use to provide CRM therapy. However, the present subject matter is not limited to a particular number of electrode sites. One or more electrodes can be positioned on a lead, and one or more leads can be used. Each electrode may include its own pulse generator and sense circuitry. However, the present subject matter is not so limited. The pulse generating and sensing functions can be multiplexed to function with multiple electrodes.

The NS therapy section 1037 includes components, under the control of the controller, to stimulate a baroreceptor and sense ANS parameters associated with nerve activity, and in some embodiments sense surrogates of ANS parameters such as blood pressure and respiration. Examples of NS therapy include, but are not limited to, therapies to treat hypertension, epilepsy, obesity and breathing disorders. Three interfaces 1042 are illustrated for use to provide ANS therapy. However, the present subject matter is not limited to a particular number interfaces, or to any particular stimulating or sensing functions. Pulse generators 1043 are used to provide electrical pulses to an electrode for use to stimulate a baroreceptor site. According to various embodiments, the pulse generator includes circuitry to set, and in some embodiments change, the amplitude of the stimulation pulse, the frequency of the stimulation pulse, the burst frequency of the pulse, and/or the morphology of the pulse such as a square wave, triangle wave, sinusoidal wave, and waves with desired harmonic components to mimic white noise or other signals. Sense circuits 1044 are used to detect and process signals from a sensor, such as a sensor of nerve activity, pulsatile parameters, blood pressure, respiration, and the like. The interfaces 1042 are generally illustrated for use to communicate between the controller 1023 and the pulse generator 1043 and sense circuitry 1044. Each interface, for example, may be used to control a separate lead. Various embodiments of the NS therapy section only include a pulse generator to stimulate baroreceptors. The NS therapy section is capable of providing AHT therapy to treat hypertension, for example.

Embodiments of the NS therapy section modify therapy based on electrophysiological parameters such as heart rate, minute ventilation, atrial activation, ventricular activation, and cardiac events. Embodiments of the CRM therapy section modify therapy based on data received from the NS therapy section, such as mean arterial pressure, systolic and diastolic pressure, and baroreflex stimulation rate.

A system according to these embodiments can be used to augment partially successful treatment strategies. As an example, undesired side effects may limit the use of some pharmaceutical agents. The combination of a system according to these embodiments with reduced drug doses may be particularly beneficial.

According to various embodiments, the lead(s) and the electrode(s) on the leads are physically arranged with respect to the heart in a fashion that enables the electrodes to properly transmit pulses and sense signals from the heart, and with respect to baroreceptors, such as nerve endings and nerve trunks, to stimulate the baroreflex. As there may be a number of leads and a number of electrodes per lead, the configuration can be programmed to use a particular electrode or electrodes. According to various embodiments, the baroreflex is stimulated by stimulating afferent nerve trunks.

Figure 11:
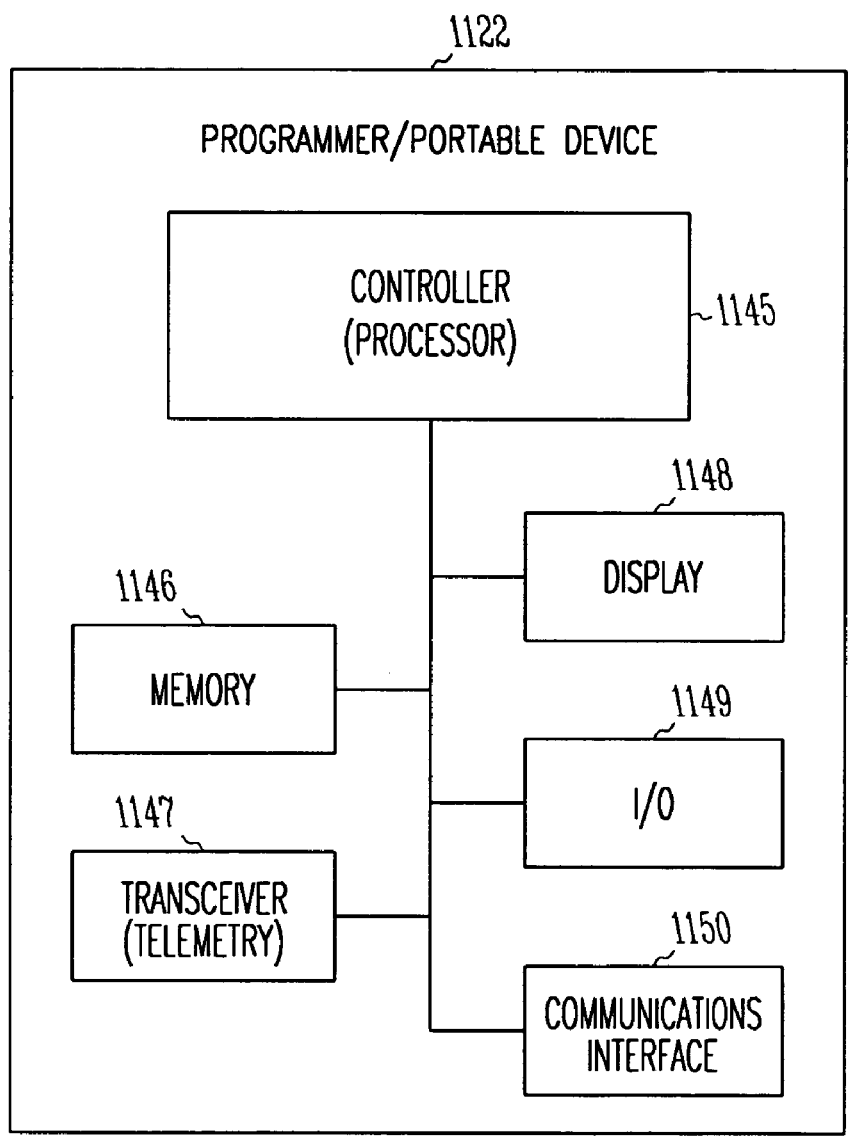
FIG. 11 illustrates a programmer such as illustrated in the system of FIG. 8 or other external device to communicate with the implantable medical device(s), according to various embodiments of the present subject matter.

FIG. 11 illustrates a programmer 1122, such as the programmer 922 illustrated in the systems of FIG. 9, or other external device to communicate with the implantable medical device(s) 921, according to various embodiments of the present subject matter. An example of another external device includes Personal Digital Assistants (PDAs) or personal laptop and desktop computers in an Advanced Patient Management (APM) system. The illustrated device 1122 includes controller circuitry 1145 and a memory 1146. The controller circuitry 1145 is capable of being implemented using hardware, software, and combinations of hardware and software. For example, according to various embodiments, the controller circuitry 1145 includes a processor to perform instructions embedded in the memory 1146 to perform a number of functions, including communicating data and/or programming instructions to the implantable devices. The illustrated device 1122 further includes a transceiver 1147 and associated circuitry for use to communicate with an implantable device. Various embodiments have wireless communication capabilities. For example, various embodiments of the transceiver 1147 and associated circuitry include a telemetry coil for use to wirelessly communicate with an implantable device. The illustrated device 1122 further includes a display 1148, input/output (I/O) devices 1149 such as a keyboard or mouse/pointer, and a communications interface 1150 for use to communicate with other devices, such as over a communication network.

The above-described functions of a system, whether implemented in two separate and distinct implantable devices or integrated as components into one or more implantable devices, include, but are not limited to, processes for monitoring nerve traffic as part of a closed-loop neural stimulation system to continuously deliver appropriate neural stimulation. Processes can be performed by a processor executing computer-readable instructions embedded in memory, for example.

The present subject matter provides neural stimulation using lead(s) that can be used to provide neural stimulation, and/or to detect and monitor nerve traffic. The lead is adapted to be connected to a device, such as an implantable neural stimulation device or integrated into a CRM device. The device processes the nerve signal with appropriate amplification and filtering for the low amplitude and high noise level associated with the nerve signal. Various embodiments provide a signal processing module that can include a wavelet transformation or other noise reduction algorithm. Recorded nerve traffic is processed with a detection algorithm adapted to identify the features of the signal, such as the pattern and intensity of the nerve traffic. The signal features are used to determine desired neural stimulation parameters, such as duration, frequency and amplitude.

A neural stimulation lead can be placed in a number of appropriate locations. For example, various lead embodiments to stimulate a baroreflex are expandable, and are adapted to be placed in the pulmonary artery in the proximity of a high concentration of baroreceptors. Various lead embodiments are adapted to stimulate nerve endings in cardiac fat pads. Some lead embodiments are transvascular leads placed proximal to a cardiac fat pad. Some lead embodiments place an epicardial lead in a cardiac fat pad. Various lead embodiments include a cuff electrode adapted to be placed around a nerve, such as the aortic, carotid or vagus nerve. Other leads can be placed in other neural stimulation and neural sensing locations to perform baroreflex or other therapy.

The closed-loop neural stimulation can be implemented at a same site or at different sites. In embodiments of a same site implementation, a lead is placed in a baroreceptor field, in a cardiac fat pad, or around or proximate to a nerve trunk (such as the aortic, carotid or vagus nerve). The nerve traffic is detected and monitored with appropriate amplification and filtering characteristics. The pattern and/or intensity of nerve traffic is used to determine neural stimulation parameters, such as duration, frequency, and/or amplitude, at the same site. In embodiments of a different site implementation, two neural leads are placed in different locations, such as one lead in the fat pad and one lead around the vagus nerve, for example. Nerve traffic at one site is used to guide neural stimulation at the second site. Various device embodiments monitor and record autonomic nerve traffic data as part of an APM system.

Various device embodiments include an amplification and filtering circuit adapted to process and monitor nerve traffic. The device includes a signal processing module that includes a noise reduction algorithm such as a wavelet transformation.

Figure 12A:
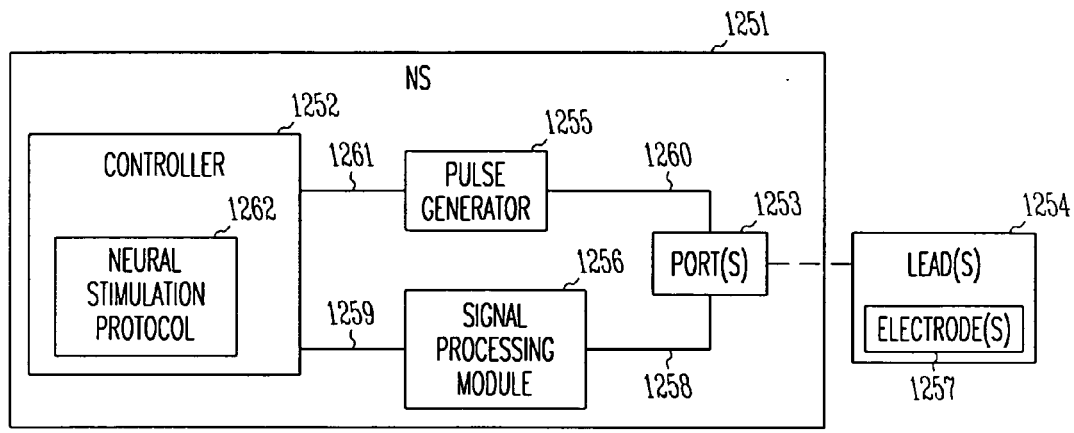
FIGS. 12A-12C illustrate neural stimulators, according to various embodiments of the present subject matter.
Figure 12B:
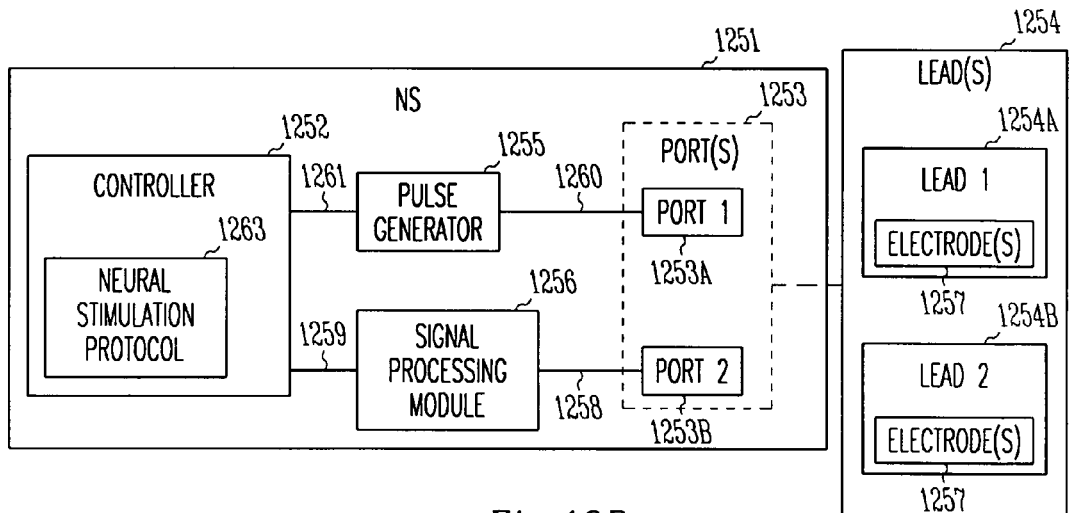
Figure 12C:
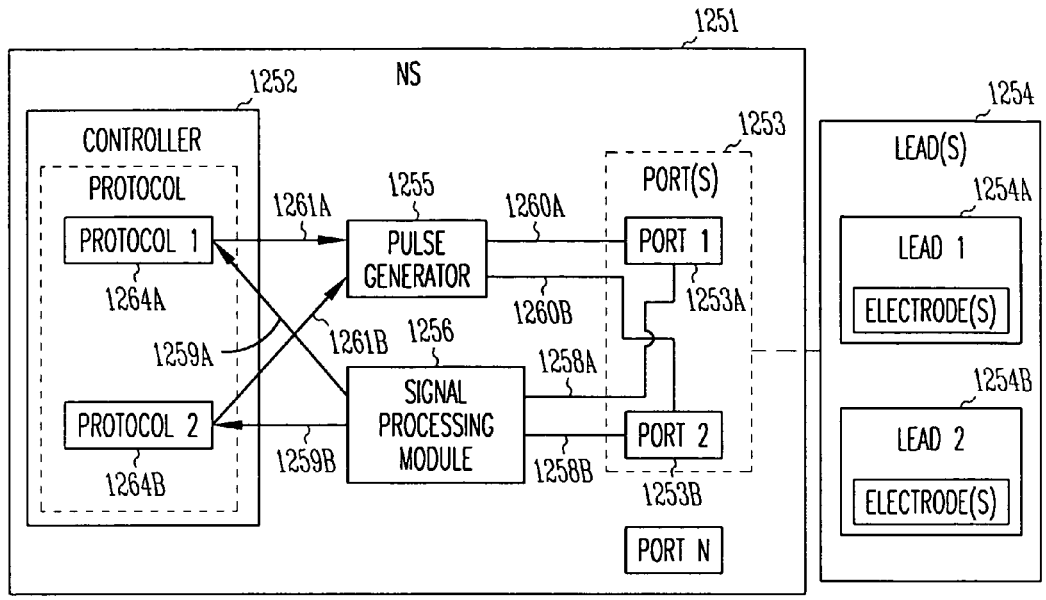

FIGS. 12A-12C illustrate neural stimulators, according to various embodiments of the present subject matter. FIGS. 12A-12C illustrate a few logical arrangements for providing closed-loop neural stimulation based on sensed neural traffic. Other logical arrangements are capable of being implemented, such as are illustrated in FIGS. 16A-16D.

The neural stimulator device 1251 illustrated in FIG. 12A includes a controller 1252, at least one port 1253 to connect at least one lead 1254, a pulse generator 1255 connected to the controller and to the port, and a signal processing module 1256 connected to the controller and to the port. The at least one lead includes at least one electrode 1257 for stimulation and/or sensing. The signal processing module 1256 is adapted to receive and process a nerve traffic signal on path 1258 from the lead into a signal indicative of the nerve traffic on signal path 1259. The pulse generator 1255 is adapted to provide a neural stimulation signal to the lead on signal path 1260 based on a control signal from the controller 1252 on path 1261. The controller is adapted to implement a stimulation protocol 1262, which in conjunction with the pulse generator, provides the neural stimulation signal with desired neural stimulation parameters based on the signal indicative of the nerve traffic received from the lead. For example, the amplitude, frequency, burst frequency, burst duration, duty cycle, morphology, pulse width, and various combinations thereof, for the neural stimulation signal are capable of being adjusted based on the signal indicative of nerve traffic. The illustrated device is capable of sensing and stimulating using the same lead. Thus, the closed-loop system can be based on sensed nerve traffic at or near the same site where neural stimulation is applied.

The neural stimulator device 1251 illustrated in FIG. 12B includes a controller 1252, at a first port 1253A to connect a first lead 1254A and a second port 1253B to connect a second lead 1254B, a pulse generator 1255 connected to the controller and to the first port, and a signal processing module 1256 connected to the controller and to the second port. The leads include at least one electrode 1257. The signal processing module 1256 is adapted to receive and process a nerve traffic signal on path 1258 from the second lead 1254B into a signal indicative of the nerve traffic on signal path 1259. The pulse generator 1255 is adapted to provide a neural stimulation signal to the lead on signal path 1260 based on a control signal from the controller 1252 on path 1261. The controller is adapted to implement a stimulation protocol 1263, which in conjunction with the pulse generator, provides the neural stimulation signal with desired neural stimulation parameters to the first lead based on the signal indicative of the nerve traffic received from the second lead. Thus, nerve traffic at one site is capable of being used to guide neural stimulation at another site. For example, the amplitude, frequency, burst frequency, burst duration, duty cycle, morphology, pulse width, and various combinations thereof, for the neural stimulation signal are capable of being adjusted based on the signal indicative of nerve traffic.

The neural stimulator device 1251 illustrated in FIG. 12C includes a controller 1252, a first port 1253A to connect a first lead 1254A and a second port 1253B to connect a second lead 1254B, a pulse generator 1255 connected to the controller via path 1261A and 1261B and operably connected to the first and second ports via paths 1258A and 1258B to perform a desired stimulation, and a signal processing module 1256 connected to the controller 1252 via path 1259A and 1259B and operably connected to the first and second ports to provide desired sensing. The leads include at least one electrode. The signal processing module 1256 is adapted to receive and process a nerve traffic signal on path 1258A from the first lead and on path 1258B from the second lead into a signals indicative of the nerve traffic sensed by the first and second leads, respectively. The pulse generator 1255 is adapted to provide a neural stimulation signal to the first lead on signal path 1260A based on a control signal from the controller 1252 on path 1261A, and to the second lead on signal path 1260B based on a control signal from the controller 1252 on path 1261B. The controller is adapted to implement a stimulation protocol or protocols 1264A and 1264B, which in conjunction with the pulse generator, provides the neural stimulation signal with desired neural stimulation parameters to the first lead based on the signal indicative of the nerve traffic received from the second lead, and further provides the neural stimulation with desired neural stimulation parameters to the second lead based on the signal indicative of the nerve traffic received from the first lead. For example, the amplitude, frequency, burst frequency, burst duration, duty cycle, morphology, pulse width, and various combinations thereof, for the neural stimulation signal are capable of being adjusted based on the signal indicative of nerve traffic. As illustrated in FIG. 12C, additional ports (Port N) can be included for use in sensing and/or stimulation.

According to various embodiments, the signal processing module is adapted to provide a signal or signals indicative of a nerve traffic pattern and/or nerve traffic intensity as an indication of the nerve traffic. According to various embodiments, the signal processing module is adapted to implement noise reduction algorithm, such as a wavelet transformation, to identify features of a nerve traffic signal that is characterized by a low amplitude and high noise level. According to various embodiments, the signal processing module includes an amplifier, such as an amplifier with a gain within a range of approximately 1,000 to approximately 99,000. According to various embodiments, the signal processing module includes a bandpass filter, such as a filter to pass frequencies in a range from approximately 30 Hz to approximately 3,000 Hz.

Figure 13:
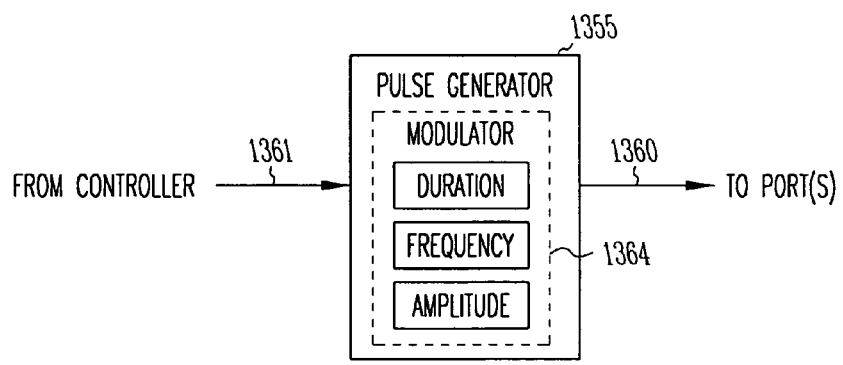
FIG. 13 illustrates a pulse generator, such as shown in the neural stimulators of FIGS. 12A-12C, according to various embodiments of the present subject matter.

FIG. 13 illustrates a pulse generator, such as shown in the neural stimulators of FIGS. 12A-12C, according to various embodiments of the present subject matter. The illustrated pulse generator 1355 is adapted to receive a control signal via path 1361 from a controller and to provide a neural stimulation signal via path 1360 to lead(s) via port(s). The illustrated pulse generator includes a modulator 1364 that is responsive to the control signal from the controller to change one or more parameters of the stimulation signal such as the amplitude, frequency, burst frequency, burst duration, duty cycle, morphology, pulse width of the stimulation signal.

Figure 14:
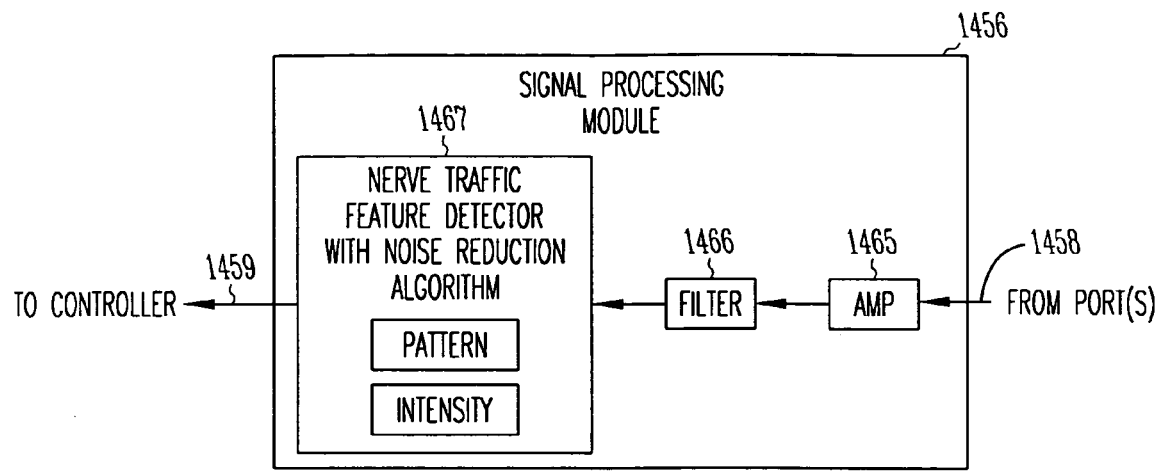
FIG. 14 illustrates a signal processing module, such as shown in the neural stimulators of FIGS. 12A-12C, according to various embodiments of the present subject matter.

FIG. 14 illustrates a signal processing module, such as shown in the neural stimulators of FIGS. 12A-12C, according to various embodiments of the present subject matter. The illustrated signal processing module 1456 is adapted to receive a nerve traffic signal via path 1458 and port(s) from lead(s) and to provide a signal indicative of the nerve traffic via path 1459 to the controller. Various embodiments include an amplifier 1465 and filter 1466 adapted to process the nerve activity into a signal conditioned for discrimination or other processing. Various amplifier embodiments provide a gain within a range of approximately 1,000 to 99,000. Various filter embodiments pass frequencies in a range from approximately 30 Hz to approximately 3,000 Hz. The illustrated signal processing module further includes a nerve traffic feature detector 1467, also referred to as a discriminator, to process the amplified and filtered signal to provide a signal indicative of the nerve traffic to the controller. Various embodiments implement a noise reduction algorithm, such as a wavelet transformation, for use in discriminating the signal. Various embodiments of the nerve traffic feature detector discriminate a noise traffic pattern feature and/or a noise traffic intensity feature; and send these signals to the controller for use to guide the neural stimulation.

Figure 15:
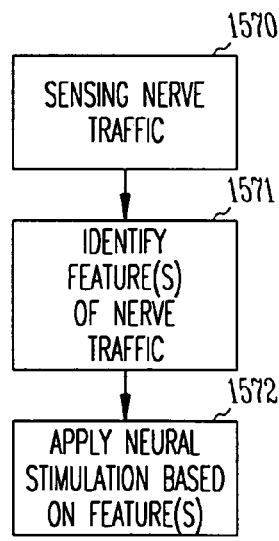
FIG. 15 illustrates a method for closed-loop stimulation, according to various embodiments of the present subject matter.

FIG. 15 illustrates method for closed-loop stimulation, according to various embodiments of the present subject matter. At 1570, nerve traffic is sensed. At 1571, one or more features of the nerve traffic is identified. Various embodiments for identifying the feature(s) of the nerve traffic include implementing a noise reduction algorithm, such as a wavelet transformation. Examples of identified features include the pattern and intensity of the nerve traffic. In various embodiments, discriminating the signal to identify features of the nerve traffic signal includes rectifying and applying a threshold to the nerve traffic signal. In various embodiments, the discriminated signal is integrated using, for example, an R-C Integrator 0.1 sec, to obtain a value for the nerve traffic activity over a 100 millisecond period of time. At 1572, neural stimulation is applied based on one or more features identified at 1571. In various embodiments, a controller implements a stimulation protocol to change at least one parameter, such as the amplitude, frequency, burst frequency, burst duration, duty cycle, morphology, pulse width, and various combinations thereof, of the stimulation signal.

FIGS. 16A-16D illustrate various closed-loop control systems implemented by various neural stimulation device embodiments. The neural stimulation device embodiment 1651A illustrated in FIG. 16A neural stimulates and senses nerve traffic at the same site. For example, a nerve, nerve ending or other site is stimulated during a first time period, and is sensed during a second time period. The sensed nerve traffic is used to adjust subsequent neural stimulations.

Figure 16A:
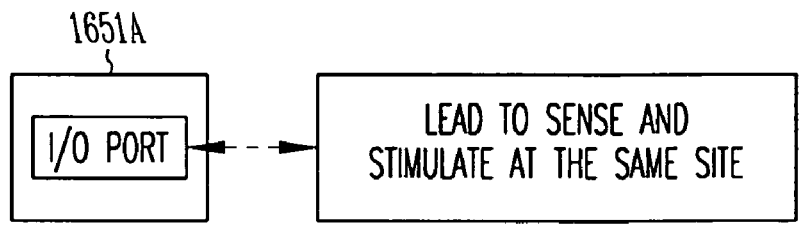
FIGS. 16A-16D illustrate various closed-loop control systems implemented by various neural stimulation device embodiments.
Figure 16B:
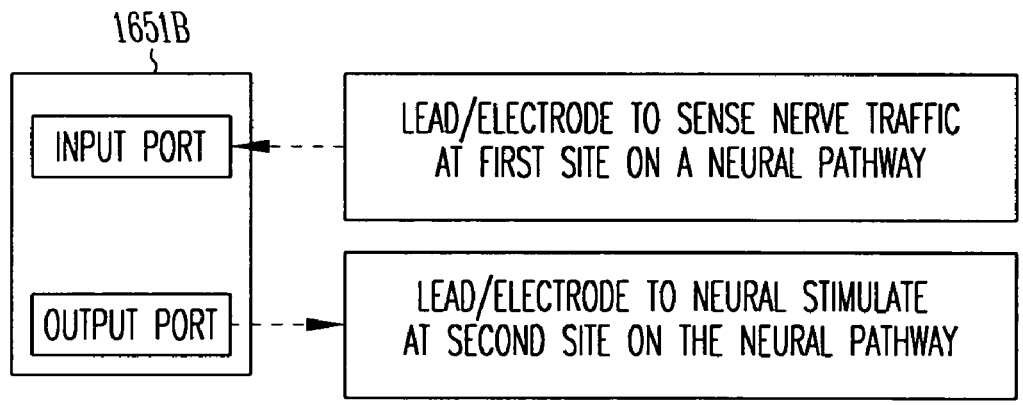

The neural stimulation device embodiment 1651B illustrated in FIG. 16B neural stimulates a first site (e.g. nerve ending or nerve) on a neural pathway, and senses nerve traffic at a second site (e.g. nerve ending or nerve) on the same neural pathway. Thus, a vagus nerve trunk, by way of example and not by way of limitation, is stimulated and the resulting nerve traffic on the vagus nerve trunk is capable of being simultaneously sensed to provide feedback to adjust the neural stimulation.

Figure 16C:
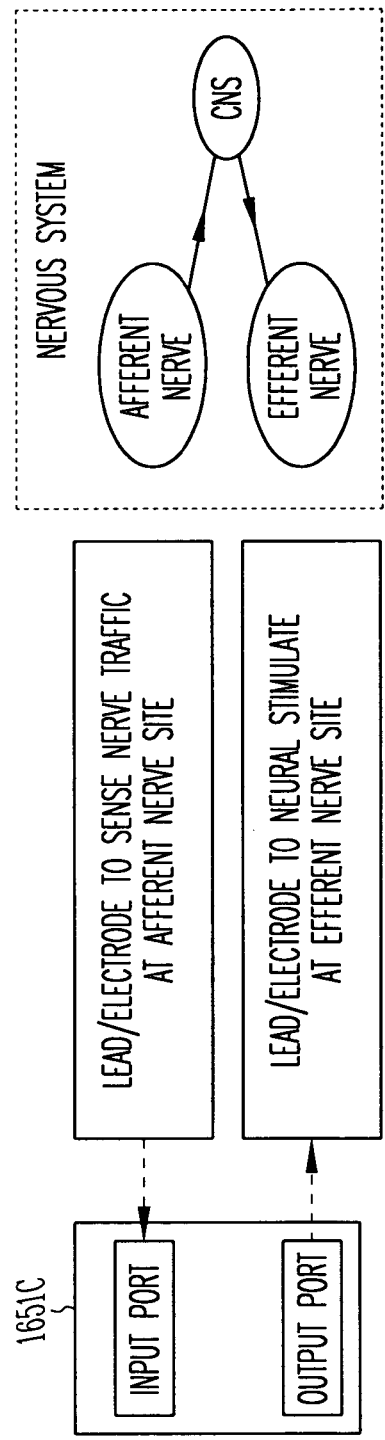

The neural stimulation device embodiment 1651C illustrated in FIG. 16C senses nerve traffic at an afferent nerve site, and neural stimulates at an efferent nerve site. In this embodiment, the neural stimulation device bypasses the central nervous system (CNS). In a healthy nervous system, the CNS receives nerve signals from afferent nerves and appropriately responds by sending appropriate nerve signals to effectors over efferent nerves. Such a system can be used to treat dysautomia, a condition where the autonomic nervous system (ANS) is dysfunctional, by bypassing the CNS by sensing afferent nerves and stimulating efferent nerves. Dysautomia includes Postural Orthostatic Tachycardia Syndrome (POTS), Neurocardiogenic Syncope (NCS), Pure Autonomic Failure (PAF) and Multiple System Atrophy (MSA). Thus, such a system bypasses the CNS physiologic feedback for certain neural functions to override dysfunctions of the autonomic nervous system.

Figure 16D:
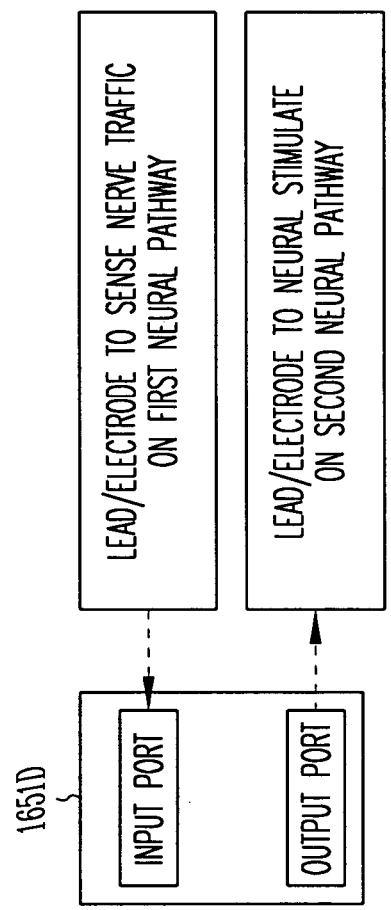

The neural stimulation device embodiment 1651D illustrated in FIG. 16D senses nerve traffic at a first site on a first neural pathway, and neural stimulates at a second site on a second neural pathway. Thus, by way of example and not by way of limitation, nerve activity associated with baroreceptors can be used to provide an indication of blood pressure, and heart rate can be appropriately controlled with appropriate neural stimulation of the SA cardiac fat pad.

The sympathetic and parasympathetic nervous systems have clearly defined sensory components that provide input to the central nervous system and play an important role in autonomic reflexes. In addition, some sensory fibers that project to the spinal cord also send a branch to autonomic ganglia, thus forming reflex circuits that control some visceral autonomic functions. A reflex has been defined as a relatively stereotyped, or repeatable, movement or response elicited by a stimulus applied to the periphery, transmitted to the central nervous system and then transmitted back out to the periphery. Some reflexes are nearly the same each time they are repeated. However, no activity of an organism is fixed and independent of either the state or the history of the organism. Most reflexes involve the simplest of neural circuits, some only two or a few neurons; but many reflexes are complex and are not fully understood.

Some reflexes serve protective functions, like the eyeblink reflex. Some reflexes act as control systems to maintain homeostasis in some bodily systems. In a control system, information more-or-less continuously flows from the controlled element back to the device that controls it. The controlled system has an input that interacts with influences from outside the system, called disturbances, in producing the output of the system. A sensor is a device that measures the output of the system, and its measurement is the feedback signal to the error detector, also referred to herein as a comparator. The feedback signal is compared with the control signal (the signal that specifies the intended output) by the error detector, which, when it finds a difference between the two signals, sends an error signal to the controller to reduce the amount of error. The actual output is brought closer to the intended output, the new output is again sensed by the sensor, and a new correction is made.

Figure 17:
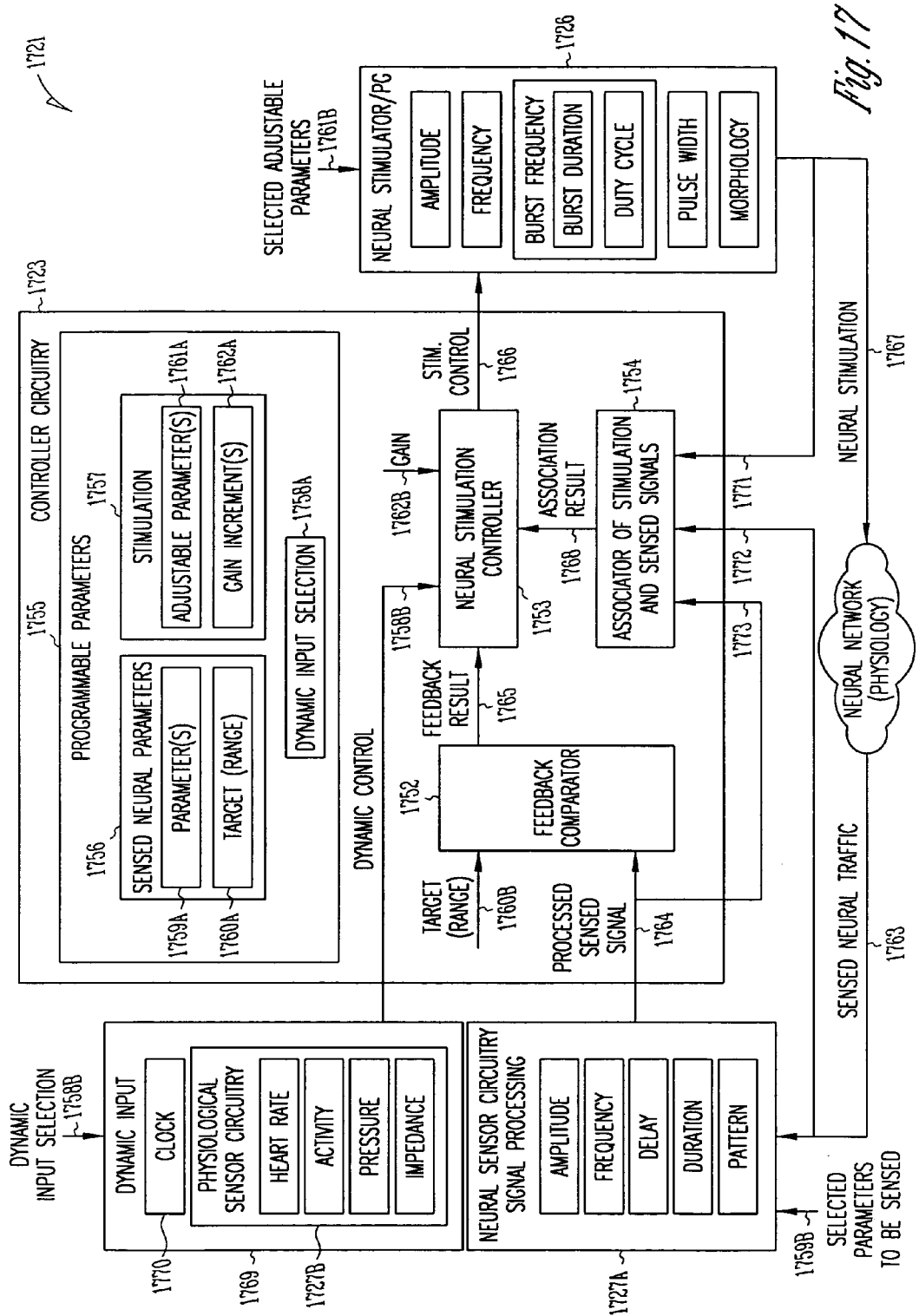
FIG. 17 illustrates an embodiment of a control system for an embodiment of a implantable medical device (IMD) which senses neural activity within the autonomic nervous system (ANS) to control neural stimulation of a neural target within the ANS.

FIG. 17 illustrates an embodiment of a control system for an embodiment of a implantable medical device (IMD) which senses neural activity within the autonomic nervous system (ANS) to control neural stimulation of a neural target within the ANS. Those of ordinary skill will understand, upon reading and comprehending this disclosure, that the functions illustrated and described with respect to the IMD 1721 of FIG. 17 can be provided by the IMD embodiment 921B generally illustrated FIG. 9B and the IMD embodiment generally illustrated in FIG. 10. With reference to FIG. 17, the IMD 1721 includes controller circuitry 1723, a neural stimulator 1726 which can also be referred to as a pulse generator, and sensor circuits illustrated as neural sensor circuitry and signal processing 1727A and physiological sensor circuitry 1727B. The illustrated controller 1723 includes a feedback comparator 1752 which can be referred to as an error detector, and a neural stimulation controller 1753. Some embodiments of the controller 1723 include an associator 1754 of stimulation and sensed signals.

The illustrated controller 1723 also includes a memory or register 1755 where values for various parameters can be programmed by an external programmer using a transceiver, such as generally illustrated in FIGS. 9B and 10. Various embodiments allow one or various combinations of two or more of the following parameter types to be programmed: sensed neural parameters 1756, stimulation parameters 1757, and dynamic input selection 1758. The illustrated sensed neural parameters 1756 includes parameter(s) to be sensed 1759A through appropriate processing of sensed neural traffic, and a desired target parameter (or desired range of parameters) 1760A. The illustrated stimulation parameters 1757 include stimulation parameter(s) to be adjusted 1761A in response to a feedback control signal, and available gain increment(s) 1762A for the adjustable stimulation parameter(s). These programmable parameters illustrated in memory 1755 provide control inputs to various modules of the device. In the illustrated embodiment, the programmable sensed parameter(s) 1759A provide a control signal 1759B to the neural sensor circuitry and signal processing 1727A that indicates the selected parameters to be sensed. The programmable adjustable stimulation parameters 1761A provide a control signal 1761B to the neural stimulator 1726 that indicates the parameters of the stimulation waveform to be adjusted. The programmable target 1760A provides a control signal 1760B to the feedback comparator 1752, the programmable gain increment 1762A provides a control signal 1762B to the neural stimulator controller 1753 that indicates an appropriate gain (positive and negative) to increment or decrement the stimulation intensity resulting from the stimulation values for the neural stimulation parameter(s). The programmable dynamic input selection 1758A provide a control signal 1758B to the neural stimulation controller to dynamically adjust the target range to account for other factors such as activity or time.

The neural sensor circuitry 1727A receives sensed neural traffic 1763 and, based on the control signal 1759B representing the desired parameter(s) to be sensed, processes the traffic to identify at least one parameter from the sensed neural traffic. Various embodiments are capable of sensing a signal amplitude, a signal frequency, a signal delay with respect to neural stimulation, duration of sensed signals, a pattern of sensed signals, and various combinations thereof. The neural sensor circuitry 1727A outputs a processed sensed signal 1764 indicative of the sensed parameters to the feedback comparator 1752, which compares the sensed parameter(s) received via signal 1764 to the target parameter or target parameter range 1760B for the sensed parameter(s). A result of the comparison is provided from the comparator 1752 to the neural stimulation controller 1753 via feedback result signal 1765. The controller 1753 receives the feedback result signal 1765, and delivers a stimulation control signal 1766 based on the feedback result signal 1765. The controller 1753 also can receive other control signals and deliver the stimulation control signal 1766 using these other control signals. The neural stimulator 1726 receives the stimulation control signal and controls the neural stimulation 1767 to adjust the intensity of stimulation if appropriate to converge to desired neural traffic 1763 as reflected by the comparison of processed sensed signal 1764 to the target 1760B. According to various embodiments, the stimulator circuitry 1726 includes modules to set or adjust any one or any combination of two or more of the following pulse features: the amplitude of the stimulation pulse, the frequency of the stimulation pulse, the burst frequency of the pulse, the wave morphology of the pulse, and the pulse width. The illustrated burst frequency pulse feature includes burst duration and duty cycle, which can be adjusted as part of a burst frequency pulse feature or can be adjusted separately without reference to a steady burst frequency.

In addition to the feedback result control input signal 1765, some embodiments of the neural stimulation controller 1753 also receive a gain control input signal 1762B used to provide the desired stimulation control signal 1766. It is noted that the intensity of the neural stimulation signal 1767 can be complexly related to the parameters of the stimulation signal. Generally, an increased amplitude of the signal increases neural stimulation. Additionally, there is a frequency window which corresponds to the highest neural stimulation intensity, and frequencies that are either higher or lower than the frequency window provide less neural stimulation. Also, stimulated neural sites can quickly adapt to steady stimulation. Thus, adjustments in stimulation intensity can correspond to a variety of adjustments to one or more of the amplitude of the stimulation pulse, the frequency of the stimulation pulse, the burst frequency of the pulse, the burst duration of the pulse, the duty cycle of the stimulation, the wave morphology of the pulse, and the pulse width. The gain control adjusts the stimulation parameter(s) to achieve a desired increment or decrement in neural stimulation intensity. According to some embodiments, the parameter adjustments are predetermined to provide the stimulation intensity adjustments. Some embodiments use an iterative protocol to determine the effects that parameter change(s) have on intensity. For example, according to some embodiments, the gain control signal 1762B controls an algorithm used to methodically adjust stimulation parameter(s) that are available for adjustment, compare the result to determine if the neural stimulation results in a result closer to the target or further from the target, and then adjust the stimulation parameter(s) again to achieve the desired increment or decrement in the neural response. The same or different parameters can be adjusted to achieve convergence on the desired nerve traffic at the sensed neural site.

In addition to the feedback result control input signal 1765, some embodiments of the neural stimulation controller 1753 also receive a dynamic control input signal used to provide the desired stimulation control signal 1766. The illustrated dynamic input 1769 includes a clock 1770 and physiological sensor circuitry 1727B. The illustrated physiological sensor circuitry includes a heart rate sensor, an activity sensor, a pressure sensor, and impedance sensor. Other physiological sensors can be used. The dynamic input 1769 enables the dynamic adjustment of the effective operating target or target range 1760B based on a clock (e.g. a circadian rhythm) and/or based on physiological parameters. Thus, for example, the dynamic input allows the target for the sensed neural traffic to be different for someone exercising in the afternoon than sleeping in the middle of the night. The dynamic input can be used in other applications. The selection of the dynamic input as well as the resulting control algorithms that use the dynamic input control signal can be programmable.

In addition to the feedback result control input signal 1765, some embodiments of the neural stimulation controller 1753 also receive an associated result control input signal 1768 from the associator 1754. The illustrated associator 1754 receives a control signal 1771 indicative of the neural stimulation 1767 provided by the neural stimulator 1726, a control signal 1772 indicative of the sensed neural traffic 1763 received at the neural sensing circuitry 1727A, and a control signal 1773 indicative of the processed sensed signal 1764. The associator provides a means for associating the sensed neural activity to a stimulation event. For example, various embodiments use signal averaging or temporal correlation to provide the association of the sensed activity to the stimulation event.

Thus, as generally illustrated by FIG. 17, a number of control system embodiments can be used. One control system embodiment defines the target operating range of the evoked response magnitude. If the evoked response is less than the target, the stimulation amplitude, frequency and/or burst duration is adjusted by one gain increment; if the evoked response is greater than the target, the stimulation amplitude, frequency and/or burst duration is adjusted by one gain decrement; and if the evoked response is within the target range, the stimulation settings are maintained.

One control system embodiment defines a target operating range of the evoked response pattern, where the pattern includes at least one of a delay, a duration and a frequency of sensed nerve traffic. If the delay is larger or the duration shorter or the frequency less than the target, the stimulation amplitude or frequency or burst duration is adjusted by one gain increment. If the delay is shorter or the duration longer or the frequency more than the target, the stimulation amplitude or frequency or burst duration is adjusted by one gain decrement.

One control system embodiment dynamically determines the operating target range using a clock or physiological sensor, such as a heart rate sensor, patient activity sensor, pressure sensor, impedance sensor, and the like. The operating range and dynamic control are programmable in some embodiments.

One control system embodiment dynamically determines the gain adjustments using a clock or physiological sensors. The gains and their dynamic control are programmable in some embodiments.

The stimulation and sensing leads can be located to position and/or sense any peripheral nerve, such as the vagus nerve, any sensory receptor regions such as a baroreceptor plexus, and ANS ganglia such as a cardiac fat pad or a sympathetic ganglion, and cardiac sympathetic branches. Some lead configuration embodiments are illustrated below.

Figure 18:
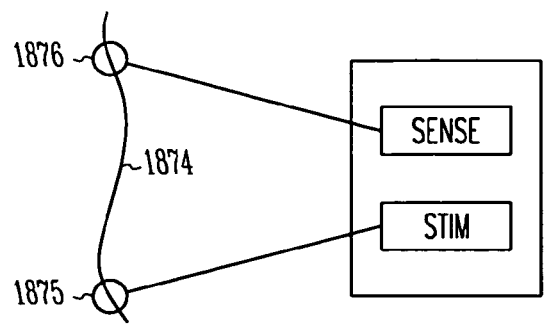
FIG. 18 illustrates an embodiment to stimulate and sense on the same peripheral nerve path.

FIG. 18 illustrates an embodiment to stimulate and sense on the same peripheral nerve path 1874. In the illustrated embodiment, one neural site 1875 on the nerve path 1874 is used to stimulate and another neural site 1876 on the same nerve path 1874 is used to sense neural traffic to determine the evoked response of the stimulation. The illustrated neural path can be either an efferent or afferent nerve. The sensed nerve traffic can be used to monitor the effectiveness of the stimulation parameters to recruit nerve traffic and to adjust the stimulation parameters to achieve the recruitment goal.

Figure 19:
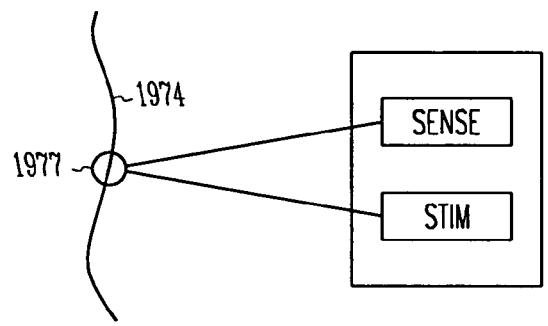
FIG. 19 illustrates an embodiment to stimulate and sense at the same neural site.

FIG. 19 illustrates an embodiment to stimulate and sense at the same neural site. The same set of electrodes 1977 can be used to stimulate the nerve path 1974 and to measure the change in ambient nerve traffic sensed after the stimulation. For example, a branch (efferent or afferent) of a reflex circuit can be stimulated with a burst, and then the branch can be sensed to determine if the ambient or intrinsic level of nerve activity increases or decreases within a specified period after the stimulation. The specified period corresponds to the reflex circuit time. The evoked reflex response magnitude can be used to determine if the stimulation needs to be increased or decreased to achieve the stimulation goal.

Figure 20:
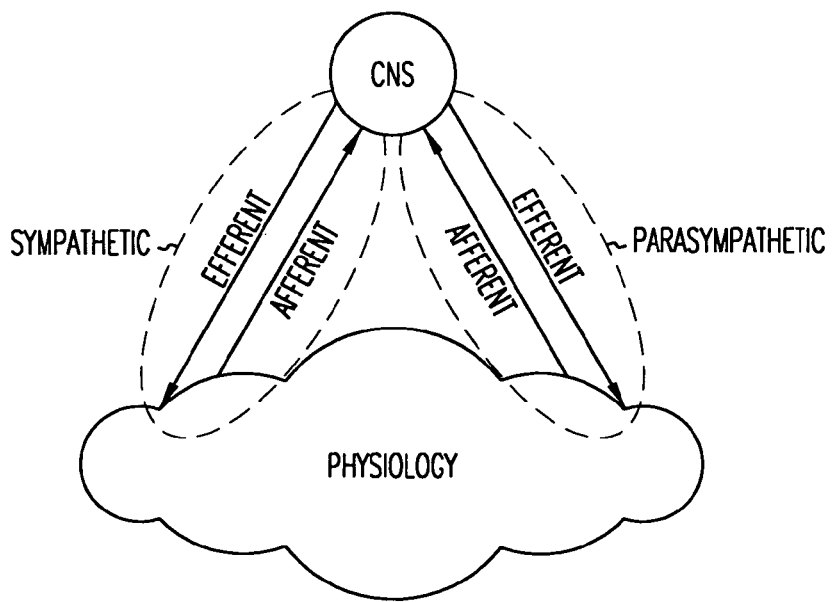
FIG. 20 illustrates efferent and afferent sympathetic nerves and efferent and afferent parasympathetic nerves within the autonomic nervous system (ANS).

FIG. 20 illustrates efferent and afferent sympathetic nerves and efferent and afferent parasympathetic nerves within the autonomic nervous system (ANS). This illustration is useful as a reference for the control system feedbacks generally illustrated in FIGS. 21A-D, 22A-D, 23A-D and 24A-D. FIG. 20 illustrates a central nervous system CNS and nerves connecting the central nervous system to physiology. The nerves include sympathetic nerves and parasympathetic nerves. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system. Both the sympathetic and parasympathetic nerves include afferent nerves which deliver neural signals toward a CNS nerve center and efferent nerves which deliver neural signals away from a CNS nerve center. Neural traffic in one nerve can affect neural traffic in another nerve through a reflex circuit in the neural network (illustrated generally as a physiology cloud as the functions associated with the sympathetic and parasympathetic nervous systems are many and can be complexly integrated with each other).

Control systems use feedback based on a comparison of the sensed response and the goal response (Feedback=Sensed−Goal). Positive feedback in a control system indicates exponential growth and divergent behavior as a positive differences becomes more positive and a negative difference becomes more negative, and negative feedback in a control system indicates maintenance of equilibrium and convergence to a goal. Thus, control systems use negative feedback to reach a stable, desired output. A representation of an operation amplifier with a differential input having positive and negative terminals is used in FIGS. 21A-D, 22A-D, 23A-D and 24A-D to illustrate positive and negative feedback from the perspective of the IMD control system.

Generally, stimulation of sympathetic nerves increases sympathetic neural activity and decreases or inhibits parasympathetic neural activity, and stimulation of parasympathetic nerves increases parasympathetic neural activity and decreases sympathetic neural activity. The ANS is used as part of the feedback loop for neural stimulators that sense neural traffic for control. The inverse relationship between parasympathetic and sympathetic activity results in the use of positive feedback, from the perspective of the IMD controls system, to converge to a goal when stimulating one of a parasympathetic nerve and a sympathetic nerve and sensing neural traffic on the other one of the parasympathetic nerve and the sympathetic nerve.

Figure 21A:
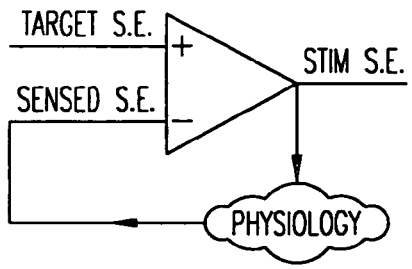
FIGS. 21A-D illustrate various control system embodiments for stimulating a sympathetic efferent nerve.
Figure 21B:
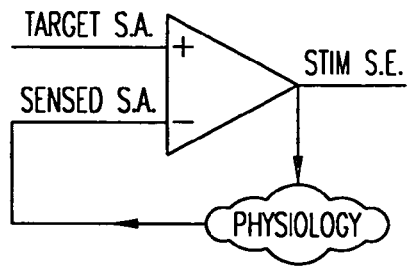
Figure 21C:
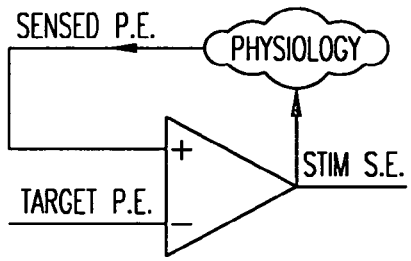
Figure 21D:
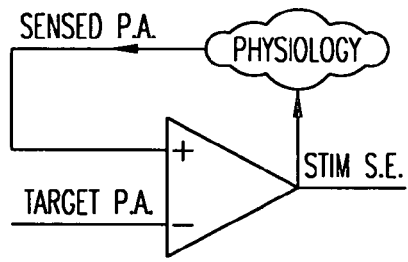

FIGS. 21A-D illustrate various control system embodiments for stimulating a sympathetic efferent nerve. FIG. 21A compares a target neural response for a sympathetic efferent (TARGET S.E.) nerve to a sensed neural response of the sympathetic efferent (SENSED S.E.) nerve to generate a stimulation signal for a sympathetic efferent nerve (STIM. S.E.). The sensed and stimulated sympathetic efferent nerves can be the same or different nerves. A reflex circuit, represented by the physiology cloud, provides a feedback for the STIM. S.E. nerve back to the SENSED S.E. nerve. As both the stimulated and sensed nerves are sympathetic nerves, the IMD controller uses negative feedback, as represented by the negative terminal on the amplifier. Thus, the stimulation will be reduced if the sensed neural traffic is too high, and will be increased if the sensed neural traffic is too low in comparison to the target. FIG. 21B compares a target neural response for a sympathetic afferent (TARGET S.A.) nerve to a sensed neural response of the sympathetic afferent (SENSED S.A.) nerve to generate a stimulation signal for a sympathetic efferent nerve (STIM. S.E.). A reflex circuit, represented by the physiology cloud, provides a feedback for the STIM. S.E. nerve back to the SENSED S.A. nerve. As both the stimulated and sensed nerves are sympathetic nerves, the IMD controller uses negative feedback, as represented by the negative terminal on the amplifier. Thus, the stimulation will be reduced if the sensed neural traffic is too high, and will be increased if the sensed neural traffic is too low in comparison to the target. FIG. 21C compares a target neural response for a parasympathetic efferent (TARGET P.E.) nerve to a sensed neural response of the parasympathetic efferent (SENSED P.E.) nerve to generate a stimulation signal for a sympathetic efferent nerve (STIM. S.E.). A reflex circuit, represented by the physiology cloud, provides a feedback for the STIM. S.E. nerve back to the SENSED P.E. nerve. Since the sensed nerve is a parasympathetic nerve and the stimulated nerve is a sympathetic nerve, the IMD controller uses positive feedback, as represented by the positive terminal on the amplifier. Thus, the stimulation will be reduced if the sensed neural traffic is too low, and will be increased if the sensed neural traffic is too high in comparison to the target. FIG. 21D compares a target neural response for a parasympathetic afferent (TARGET P.A.) nerve to a sensed neural response of the parasympathetic afferent (SENSED P.A.) nerve to generate a stimulation signal for a sympathetic efferent nerve (STIM. S.E.). A reflex circuit, represented by the physiology cloud, provides a feedback for the STIM. S.E. nerve back to the SENSED P.A. nerve. Since the sensed nerve is a parasympathetic nerve and the stimulated nerve is a sympathetic nerve, the IMD controller uses positive feedback, as represented by the positive terminal on the amplifier. Thus, the stimulation will be reduced if the sensed neural traffic is too low, and will be increased if the sensed neural traffic is too high in comparison to the target.

Figure 22A:
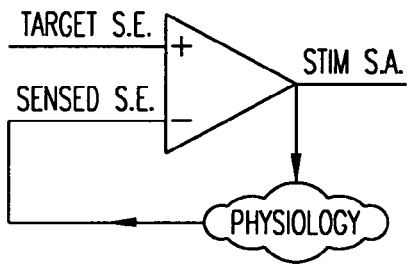
FIGS. 22A-D illustrate various control system embodiments for stimulating a sympathetic afferent nerve.
Figure 22B:
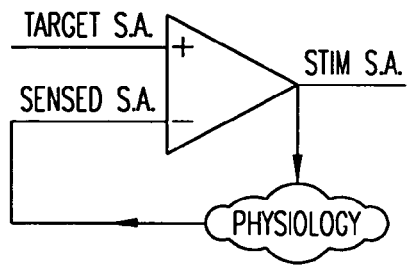
Figure 22C:
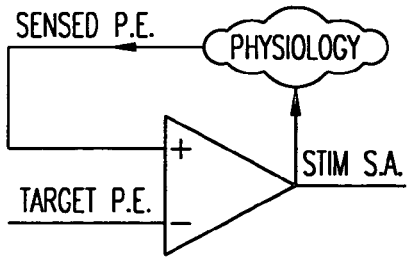
Figure 22D:
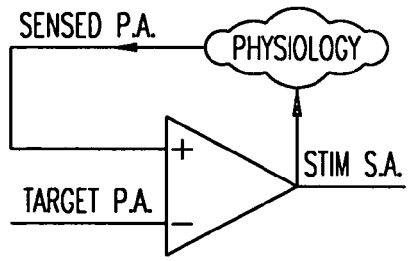

FIGS. 22A-D illustrate various control system embodiments for stimulating a sympathetic afferent nerve. FIG. 22A compares a target neural response for a sympathetic efferent (TARGET S.E.) nerve to a sensed neural response of the sympathetic efferent (SENSED S.E.) nerve to generate a stimulation signal for a sympathetic afferent nerve (STIM. S.A.). A reflex circuit, represented by the physiology cloud, provides a feedback for the STIM. S.A. nerve back to the SENSED S.E. nerve. As both the stimulated and sensed nerves are sympathetic nerves, the IMD controller uses negative feedback, as represented by the negative terminal on the amplifier. Thus, the stimulation will be reduced if the sensed neural traffic is too high, and will be increased if the sensed neural traffic is too low in comparison to the target. FIG. 22B compares a target neural response for a sympathetic afferent (TARGET S.A.) nerve to a sensed neural response of the sympathetic afferent (SENSED S.A.) nerve to generate a stimulation signal for a sympathetic afferent nerve (STIM. S.A.). The sensed and stimulated sympathetic afferent nerves can be the same or different nerves. A reflex circuit, represented by the physiology cloud, provides a feedback for the STIM. S.A. nerve back to the SENSED S.A. nerve. As both the stimulated and sensed nerves are sympathetic nerves, the IMD controller uses negative feedback, as represented by the negative terminal on the amplifier. Thus, the stimulation will be reduced if the sensed neural traffic is too high, and will be increased if the sensed neural traffic is too low in comparison to the target. FIG. 22C compares a target neural response for a parasympathetic efferent (TARGET P.E.) nerve to a sensed neural response of the parasympathetic efferent (SENSED P.E.) nerve to generate a stimulation signal for a sympathetic afferent nerve (STIM. S.A.). A reflex circuit, represented by the physiology cloud, provides a feedback for the STIM. S.A. nerve back to the SENSED P.E. nerve. Since the sensed nerve is a parasympathetic nerve and the stimulated nerve is a sympathetic nerve, the IMD controller uses positive feedback, as represented by the positive terminal on the amplifier. Thus, the stimulation will be reduced if the sensed neural traffic is too low, and will be increased if the sensed neural traffic is too high in comparison to the target. FIG. 22D compares a target neural response for a parasympathetic afferent (TARGET P.A.) nerve to a sensed neural response of the parasympathetic afferent (SENSED P.A.) nerve to generate a stimulation signal for a sympathetic afferent nerve (STIM. S.A.). A reflex circuit, represented by the physiology cloud, provides a feedback for the STIM. S.A. nerve back to the SENSED P.A. nerve. Since the sensed nerve is a parasympathetic nerve and the stimulated nerve is a sympathetic nerve, the IMD controller uses positive feedback, as represented by the positive terminal on the amplifier. Thus, the stimulation will be reduced if the sensed neural traffic is too low, and will be increased if the sensed neural traffic is too high in comparison to the target.

Figure 23A:
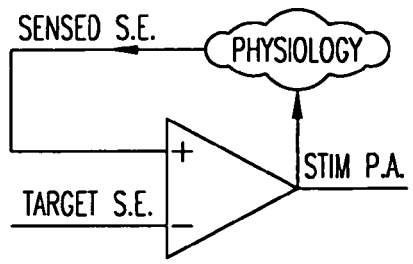
Figure 22B:
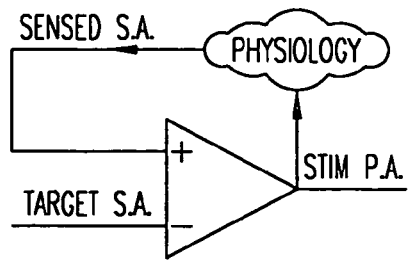
Figure 23C:
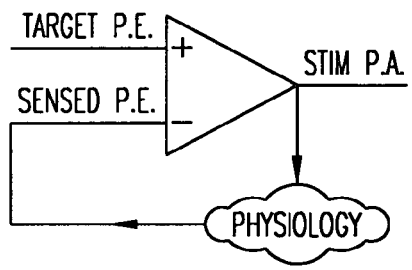
Figure 23D:
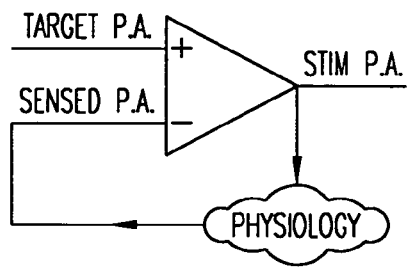

FIGS. 23A-D illustrate various control system embodiments for stimulating a parasympathetic afferent nerve. FIG. 23A compares a target neural response for a sympathetic efferent (TARGET S.E.) nerve to a sensed neural response of the sympathetic efferent (SENSED S.E.) nerve to generate a stimulation signal for a parasympathetic afferent nerve (STIM. P.A.). A reflex circuit, represented by the physiology cloud, provides a feedback for the STIM. P.A. nerve back to the SENSED S.E. nerve. Since the sensed nerve is a sympathetic nerve and the stimulated nerve is a parasympathetic nerve, the IMD controller uses positive feedback, as represented by the positive terminal on the amplifier. Thus, the stimulation will be reduced if the sensed neural traffic is too low, and will be increased if the sensed neural traffic is too high in comparison to the target. FIG. 23B compares a target neural response for a sympathetic afferent (TARGET S.A.) nerve to a sensed neural response of the sympathetic afferent (SENSED S.A.) nerve to generate a stimulation signal for a parasympathetic afferent nerve (STIM. P.A.). A reflex circuit, represented by the physiology cloud, provides a feedback for the STIM. P.A. nerve back to the SENSED S.A. nerve. Since the sensed nerve is a sympathetic nerve and the stimulated nerve is a parasympathetic nerve, the IMD controller uses positive feedback, as represented by the positive terminal on the amplifier. Thus, the stimulation will be reduced if the sensed neural traffic is too low, and will be increased if the sensed neural traffic is too high in comparison to the target. FIG. 23C compares a target neural response for a parasympathetic efferent (TARGET P.E.) nerve to a sensed neural response of the parasympathetic efferent (SENSED P.E.) nerve to generate a stimulation signal for a parasympathetic afferent nerve (STIM. P.A.). A reflex circuit, represented by the physiology cloud, provides a feedback for the STIM. P.A. nerve back to the SENSED P.E. nerve. As both the stimulated and sensed nerves are parasympathetic nerves, the IMD controller uses negative feedback, as represented by the negative terminal on the amplifier. Thus, the stimulation will be reduced if the sensed neural traffic is too high, and will be increased if the sensed neural traffic is too low in comparison to the target. FIG. 23D compares a target neural response for a parasympathetic afferent (TARGET P.A.) nerve to a sensed neural response of the parasympathetic afferent (SENSED P.A.) nerve to generate a stimulation signal for a parasympathetic afferent nerve (STIM. P.A.). The sensed and stimulated parasympathetic afferent nerves can be the same or different nerves. A reflex circuit, represented by the physiology cloud, provides a feedback for the STIM. P.A. nerve back to the SENSED P.A. nerve. As both the stimulated and sensed nerves are parasympathetic nerves, the IMD controller uses negative feedback, as represented by the negative terminal on the amplifier. Thus, the stimulation will be reduced if the sensed neural traffic is too high, and will be increased if the sensed neural traffic is too low in comparison to the target.

Figure 24A:
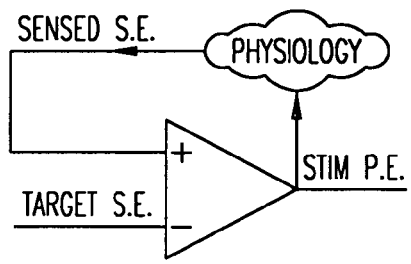
FIGS. 24A-D illustrate various control system embodiments for stimulating a parasympathetic efferent nerve.
Figure 24B:
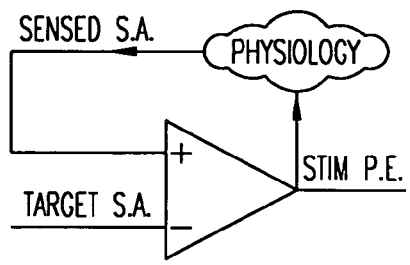
Figure 24C:
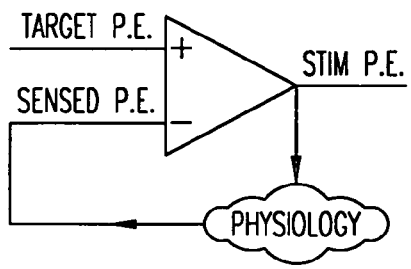
Figure 24D:
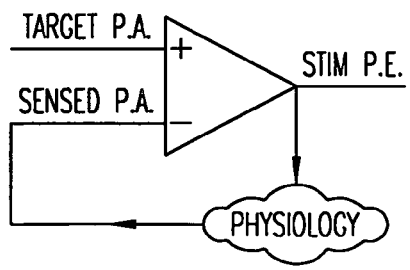

FIGS. 24A-D illustrate various control system embodiments for stimulating a parasympathetic efferent nerve. FIG. 24A compares a target neural response for a sympathetic efferent (TARGET S.E.) nerve to a sensed neural response of the sympathetic efferent (SENSED S.E.) nerve to generate a stimulation signal for a parasympathetic efferent nerve (STIM. P.E.). A reflex circuit, represented by the physiology cloud, provides a feedback for the STIM. P.E. nerve back to the SENSED S.E. nerve. Since the sensed nerve is a sympathetic nerve and the stimulated nerve is a parasympathetic nerve, the IMD controller uses positive feedback, as represented by the positive terminal on the amplifier. Thus, the stimulation will be reduced if the sensed neural traffic is too low, and will be increased if the sensed neural traffic is too high in comparison to the target. FIG. 24B compares a target neural response for a sympathetic afferent (TARGET S.A.) nerve to a sensed neural response of the sympathetic afferent (SENSED S.A.) nerve to generate a stimulation signal for a parasympathetic efferent nerve (STIM. P.E.). A reflex circuit, represented by the physiology cloud, provides a feedback for the STIM. P.E. nerve back to the SENSED S.A. nerve. Since the sensed nerve is a sympathetic nerve and the stimulated nerve is a parasympathetic nerve, the IMD controller uses positive feedback, as represented by the positive terminal on the amplifier. Thus, the stimulation will be reduced if the sensed neural traffic is too low, and will be increased if the sensed neural traffic is too high in comparison to the target. FIG. 24C compares a target neural response for a parasympathetic efferent (TARGET P.E.) nerve to a sensed neural response of the parasympathetic efferent (SENSED P.E.) nerve to generate a stimulation signal for a parasympathetic efferent nerve (STIM. P.E.). The sensed and stimulated parasympathetic efferent nerves can be the same or different nerves. A reflex circuit, represented by the physiology cloud, provides a feedback for the STIM. P.E. nerve back to the SENSED P.E. nerve. As both the stimulated and sensed nerves are parasympathetic nerves, the IMD controller uses negative feedback, as represented by the negative terminal on the amplifier. Thus, the stimulation will be reduced if the sensed neural traffic is too high, and will be increased if the sensed neural traffic is too low in comparison to the target. FIG. 24D compares a target neural response for a parasympathetic afferent (TARGET P.A.) nerve to a sensed neural response of the parasympathetic afferent (SENSED P.A.) nerve to generate a stimulation signal for a parasympathetic efferent nerve (STIM. P.E.). A reflex circuit, represented by the physiology cloud, provides a feedback for the STIM. P.E. nerve back to the SENSED P.A. nerve. As both the stimulated and sensed nerves are parasympathetic nerves, the IMD controller uses negative feedback, as represented by the negative terminal on the amplifier. Thus, the stimulation will be reduced if the sensed neural traffic is too high, and will be increased if the sensed neural traffic is too low in comparison to the target.

Figure 25:
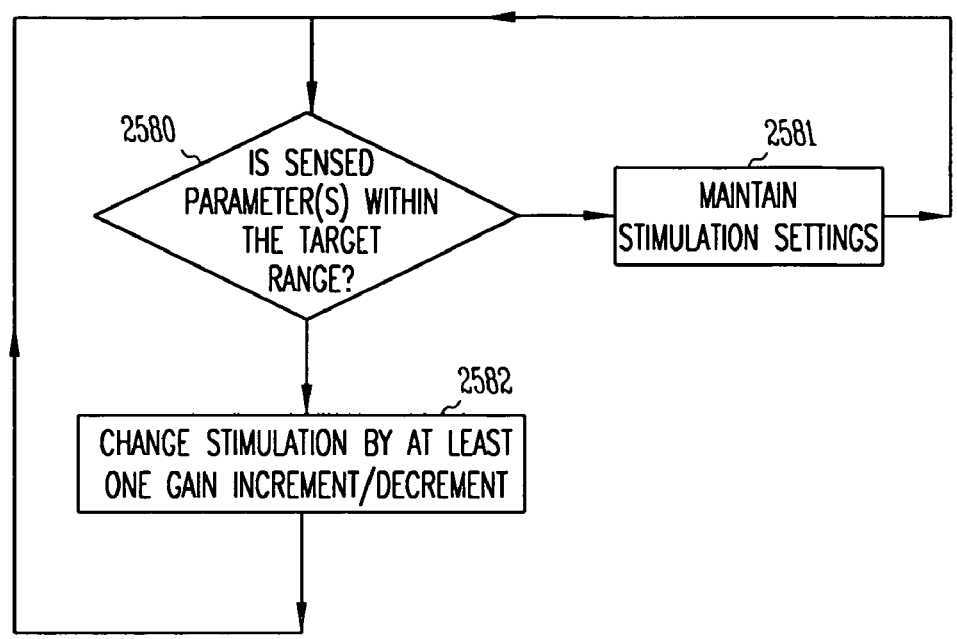
FIG. 25 illustrates an embodiment of a method to adjust neural stimulation based on sensed parameter(s).

FIG. 25 illustrates an embodiment of a method to adjust neural stimulation based on sensed parameter(s). At 2580, a determination is made as to whether the sensed parameter(s) are within the target range. The sensed parameter(s) include neural traffic parameters. In some embodiments, the sensed parameter(s) also include parameters from physiological sensors. If the parameter(s) are determined to be within a target range, the stimulation settings are maintained 2581 and the process returns to 2580. If the parameter(s) are determined to be outside of a target range, the process proceeds to 2582 to change the neural stimulation by at least one gain increment or decrement, depending on the arrangement, to move the sensed parameter(s) toward the target. Various embodiments provide other ranges above and/or below the target range; various embodiments provide a target-sub-range within the target range, and various embodiments further provide a number of other sub-ranges above and/or below the target sub-range; various embodiments provide a target sub-sub-range within a target sub-range, and various embodiments further provide other sub-sub-ranges above and/or below the target sub-sub-range. Various stimulation adjustment protocols can be used depending on the range, sub-range and sub-sub-range. Thus, for example, large adjustments can be made by adjusting one parameter (e.g. frequency) of the stimulation signal, and smaller adjustments can be made by adjusting another parameter (e.g. amplitude) of a stimulation signal.

One example of an application is an IMD to control peripheral blood pressure (hypertension). In one embodiment, baroreceptor activity is stimulated and sensed using the same electrodes. Baroreceptors can be stimulated during one cardiac cycle and sensed during another cardiac cycle (e.g. the cardiac cycle that immediately follows the cycle when stimulation occurred). Negative feedback control is used. In another embodiment, a vagus nerve or cardiac fat pad can be stimulated at a first site, and baroreceptor activity can be recorded at a second site. Negative feedback control is used for this embodiment too as the vagus nerve, cardiac fat pad, and baroreceptors are all parasympathetic sites.

Another example of an application is an IMD to treat dysautonomia (low and abnormally varying blood pressure). One embodiment senses baroreceptor activity at one site and stimulates a cardiac sympathetic nerve branch at another site. Positive feedback control is used as baroreceptors are parasympathetic sites and the cardiac sympathetic nerve branch is a sympathetic site.

Another example of an application is an IMD to treat myocardial infarction, angina, and/or heart failure. One embodiment stimulates and senses efferent or afferent evoked responses in the vagus nerve at two sites. The stimulation and sensing can be rostral stimulation and caudal sensing, or caudal stimulation and rostral sensing. Negative feedback control is used to get a target level of evoked nerve traffic. One embodiment stimulates the vagus nerve and senses sympathetic nerve traffic. Since the vagus nerve is a parasympathetic site, a positive feedback control is used to get a target level of sympathetic nerve activity.

One of ordinary skill in the art will understand that, the modules and other circuitry shown and described herein can be implemented using software, hardware, and combinations of software and hardware. As such, the term module is intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. For example, various embodiments combine two or more of the illustrated processes. Two or more sensed parameters can be combined into a composite parameter used to provide a desired neural stimulation (NS) or anti-hypertension (AHT) therapy. In various embodiments, the methods provided above are implemented as a computer data signal embodied in a carrier wave or propagated signal, that represents a sequence of instructions which, when executed by a processor cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments as well as combinations of portions of the above embodiments in other embodiments will be apparent to those of skill in the art upon reviewing the above description. The scope of the present subject matter should be determined with reference to the appended claims, along with the full scope of equivalents to which such claims are entitled.

What is claimed is:

1. A device, comprising:
   a pulse generator adapted to provide a neural stimulation signal to be applied at a neural simulation site within an autonomic nervous system (ANS);
   a signal processing module adapted to receive and process sensed neural traffic at a neural sensing site within the ANS, wherein the sensed neural traffic includes an evoked response to the neural stimulation signal applied at the neural stimulation site;
   a controller configured to provide closed-loop control of the pulse generator, wherein the controller is connected to the pulse generator and adapted to provide a neural stimulation control signal to the pulse generator to generate the neural stimulation signal and connected to the signal processing module to receive a feedback control signal indicative of the evoked nerve traffic response to the neural stimulation signal, wherein the controller is configured to provide the closed-loop control by adjusting the neural stimulation control signal to adjust at least one parameter of the neural stimulation signal to converge on a desired evoked nerve traffic response target,
   wherein the controller is further configured to dynamically adjust the closed-loop control to account for another sensed physiological parameter or time, wherein in dynamically adjusting the closed-loop control, the controller is configured to use a clock or a sensed physiological parameter to dynamically adjust the desired evoked nerve traffic response target.

2. The device of claim 1, wherein the neural stimulation site within the ANS is a parasympathetic neural stimulation site and the neural sensing site within the ANS is a parasympathetic neural sensing site, wherein the controller is configured to receive the feedback control signal as negative feedback to provide the closed-loop control to converge on the desired evoked nerve traffic response target at the parasympathetic neural sensing site.

3. The device of claim 2, wherein the parasympathetic neural stimulation site is the parasympathetic neural sensing site.

4. The device of claim 3, wherein the parasympathetic neural stimulation site and the parasympathetic neural sensing site includes a baroreceptor site.

5. The device of claim 4, wherein at least two electrodes are used to both stimulate and sense the baroreceptor site, the device further comprising a sensor to sense cardiac cycles connected to the controller, wherein the controller is adapted to neural stimulate the baroreceptor site during one cardiac cycle and sense neural activity during another cardiac cycle.

6. The device of claim 2, wherein the parasympathetic neural stimulation site is a different site than the parasympathetic neural sensing site.

7. The device of claim 6, wherein the parasympathetic neural stimulation site includes at least one of a vagus nerve and a cardiac fat pad, and the parasympathetic neural sensing site includes a baroreceptor site.

8. The device of claim 2, wherein the parasympathetic neural stimulation site includes a first site on a vagus nerve, and the parasympathetic neural sensing site includes a second site on the vagus nerve.

9. The device of claim 8, wherein one of the first site and the second site is an efferent site and the other is an afferent site.

10. The device of claim 8, wherein both the first and second sites are afferent sites on the vagus nerve.

11. The device of claim 8, wherein both the first and second sites are efferent sites on the vagus nerve.

12. The device of claim 1, wherein the neural stimulation site within the ANS is a sympathetic neural stimulation site and the neural sensing site within the ANS is a sympathetic neural sensing site, wherein the controller is configured to receive the feedback control signal as negative feedback to provide the closed-loop control to converge on the desired evoked nerve traffic response target at the sympathetic neural sensing site.

13. The device of claim 12, wherein both the neural stimulation site and the neural sensing site include a cardiac sympathetic nerve branch.

14. The device of claim 1, wherein the neural stimulation site within the ANS is a parasympathetic neural stimulation site and the neural sensing site within the ANS is a sympathetic neural sensing site, wherein the controller is configured to receive the feedback control signal as positive feedback to provide the closed-loop control to converge on the evoked nerve traffic response target at the sympathetic neural sensing site.

15. The device of claim 14, wherein the parasympathetic neural stimulation site includes a vagus nerve site.

16. The device of claim 14, wherein the parasympathetic neural stimulation site includes a baroreceptor site and the sympathetic neural sensing site includes a cardiac sympathetic nerve branch.

17. The device of claim 1, wherein the neural stimulation site within the ANS is a sympathetic neural stimulation site within the ANS and the neural sensing site is a parasympathetic neural sensing site, wherein the controller is configured to receive the feedback control signal as positive feedback to provide the closed-loop control to converge on the desired evoked nerve traffic response target at the parasympathetic neural sensing site.

18. The device of claim 17, wherein the sympathetic neural stimulation site includes a cardiac sympathetic nerve branch, and the parasympathetic neural sensing site includes a baroreceptor site.

19. The device of claim 1, wherein the controller is configured to receive a gain input control signal to provide a desired increment or decrement in neural stimulation intensity and wherein the controller is configured to increment or decrement the neural stimulation intensity, wherein the neural stimulation intensity is incremented or decremented in response to the feedback control signal.

20. The device of claim 19, wherein the controller is configured to use the clock or the sensed physiological parameter to dynamically adjust the gain.

21. The device of claim 1, wherein the controller includes an associator configured to associate the sensed neural activity to a neural stimulation event.

22. The device of claim 1, wherein the controller is configured to associate the sensed neural activity to a neural stimulation event to verify a causal relationship between sensed and stimulated neural activity, and to receive a gain input control signal to provide a desired increment or decrement in neural stimulation intensity, wherein the neural stimulation intensity is incremented or decremented in response to the feedback control signal.

23. The device of claim 1, wherein the neural simulation site is on a neural pathway and the neural sensing site is on the same neural pathway.

24. The device of claim 1, wherein the neural simulation site is at he neural sensing site.

25. The device of claim 1, wherein the controller is configured to use the clock to dynamically adjust the evoked nerve traffic response target according to a circadian rhythm.

26. The device of claim 1, wherein the controller is configured to use sensed heart rate, sensed activity, sensed pressure or sensed impedance to dynamically adjust the evoked nerve traffic response target.

27. An implantable medical device, comprising:
a neural stimulator adapted to provide a neural stimulation signal to be applied at a neural simulation site within an autonomic nervous system (ANS);
a neural sensor and signal processing module adapted to receive and process sensed neural traffic at a neural sensing site within the ANS, wherein the sensed neural traffic includes an evoked response to the neural stimulation signal applied at the neural stimulation site; and
controller circuitry configured to provide closed-loop control of the neural stimulator, wherein the controller circuitry is connected to the neural stimulator and configured to provide a neural stimulation control signal to the neural stimulator to generate the neural stimulation signal and connected to the signal processing module to receive a feedback indicative of the evoked nerve traffic response target, the controller including a feedback comparator and a neural controller, wherein the feedback comparator is configured to receive an evoked nerve traffic response signal from the neural sensor and signal processing module, to receive a target for the evoked nerve traffic response signal, and to compare the evoked nerve traffic response signal to the target and generate a corresponding feedback signal, the neural controller configured to receive the feedback signal and generate the stimulation control signal using the feedback signal,
wherein the controller is further configured to dynamically adjust the closed-loop control of the neural stimulator to account for another sensed physiological parameter or time, wherein in dynamically adjusting the closed-loop control, the controller is configured to use a clock or a sensed physiological parameter to dynamically adjust the target for the evoked nerve traffic response.

28. The device of claim 27, further comprising an associator to produce an associated result control signal verifying a causal relationship between sensed and stimulated neural activity.

29. The device of claim 28, wherein the controller circuitry includes memory adapted to store programmable parameters related to sensing neural traffic, providing neural stimulation, and generating the dynamic control signal.

30. The device of claim 27, wherein the controller is configured to dynamically adjust the target for the evoked nerve traffic response signal according to a circadian rhythm.

31. The device of claim 27, wherein the controller is configured to dynamically adjust the target for the evoked nerve traffic response signal based on sensed heart rate, sensed activity, sensed pressure or sensed impedance.

32. A method, comprising:
- sensing nerve traffic at a first autonomic nervous system (ANS) site, wherein the sensed neural traffic includes an evoked nerve traffic response to the neural stimulation signal applied at the neural stimulation site;
- using a clock or a sensed physiological parameter to dynamically adjust a desired evoked nerve traffic response target;
- generating a feedback signal indicative of the evoked nerve traffic response at the first ANS site;
- generating a neural stimulation control signal with stimulation settings using the feedback signal and the desired evoked nerve traffic response target; and
- generating a neural stimulation signal with a controlled neural stimulation intensity at a second ANS site using the neural stimulation control signal.

33. The method of claim 32, wherein the desired evoked nerve traffic response target is a target range, and generating a neural stimulation control signal includes:
- maintaining the stimulation settings of the neural stimulation control signal if the the evoked nerve traffic response at the first ANS site is within the evoked nerve traffic response target range; and
- adjusting the stimulation settings of the neural stimulation control signal if the evoked nerve traffic response at the first ANS site is not within the evoked nerve traffic response target range.

34. The method of claim 32, further comprising verifying a causal relationship between sensed activity and stimulation events.

35. The method of claim 32, wherein both the first ANS site and the second ANS site include a sympathetic site, and generating the neural stimulation control signal using the feedback signal includes providing negative feedback control using the feedback signal.

36. The method of claim 32, wherein both the first ANS site and the second ANS site include a parasympathetic site, and generating the neural stimulation control signal using the feedback signal includes providing negative feedback control using the feedback signal.

37. The method of claim 32, wherein one of the first ANS site and the second ANS site includes a parasympathetic site and the other of the first ANS site and the second ANS site includes a sympathetic site, and generating the neural stimulation control signal using the feedback signal includes providing positive feedback control using the feedback signal.

38. The method of claim 32, wherein using a clock or a sensed physiological parameter to dynamically adjust a desired the evoked nerve traffic response target includes using the clock to dynamically adjust the desired evoked nerve traffic response target according to a circadian rhythm.

39. The method of claim 32, wherein using a clock or a sensed physiological parameter to dynamically adjust a desired evoked nerve traffic response target includes using sensed heart rate, sensed activity, sensed pressure or sensed impedance to dynamically adjust the evoked nerve traffic response target for the desired sensed neural traffic.

* * * * *